(12) United States Patent
Jitsuhara et al.

(10) Patent No.: US 10,605,804 B2
(45) Date of Patent: Mar. 31, 2020

(54) ANALYSIS METHOD, ANALYZER, AND ANALYSIS SYSTEM

(71) Applicant: Sysmex Corporation, Kobe-shi, Hyogo (JP)

(72) Inventors: Kosuke Jitsuhara, Kobe (JP); Jianyin Lu, Kobe (JP)

(73) Assignee: SYSMEX CORPORATION (JP)

( * ) Notice: Subject to any disclaimer, the term of this patent is extended or adjusted under 35 U.S.C. 154(b) by 129 days.

(21) Appl. No.: 15/608,358

(22) Filed: May 30, 2017

(65) Prior Publication Data

US 2017/0343542 A1 Nov. 30, 2017

(30) Foreign Application Priority Data

May 31, 2016 (JP) ................. 2016-109628

(51) Int. Cl.
| | |
|---|---|
| *G01N 33/543* | (2006.01) |
| *G01N 15/14* | (2006.01) |
| *B01L 3/00* | (2006.01) |
| *G01N 35/00* | (2006.01) |
| *G01N 21/64* | (2006.01) |
| *G06T 7/00* | (2017.01) |

(52) U.S. Cl.
CPC ........ *G01N 33/54326* (2013.01); *B01L 3/502* (2013.01); *B01L 3/502761* (2013.01); *G01N 15/1484* (2013.01); *G01N 21/6428* (2013.01); *G01N 33/54366* (2013.01); *G01N 35/0098* (2013.01); *G06T 7/0012* (2013.01); *B01L 2200/025* (2013.01); *B01L 2200/143* (2013.01); *B01L 2300/0654* (2013.01); *B01L 2300/087* (2013.01); *B01L 2300/0816* (2013.01); *B01L 2300/168* (2013.01); *B01L 2400/043* (2013.01); *G01N 2015/1465* (2013.01); *G01N 2021/6439* (2013.01); *G01N 2201/0636* (2013.01); *G06T 2207/10088* (2013.01); *G06T 2207/30024* (2013.01)

(58) Field of Classification Search
None
See application file for complete search history.

(56) References Cited

U.S. PATENT DOCUMENTS

| | | | |
|---|---|---|---|
| 5,637,469 A | 6/1997 | Wilding et al. | |
| 7,736,891 B2 * | 6/2010 | Nelson | G01N 33/558 422/68.1 |
| 2007/0275415 A1 | 11/2007 | Srinivasan et al. | |
| 2010/0062415 A1 * | 3/2010 | Schwoebel | G01N 21/07 435/5 |
| 2011/0221438 A1 * | 9/2011 | Goodwill | G01R 33/10 324/301 |
| 2012/0077688 A1 * | 3/2012 | Bergo | G01N 33/6845 506/9 |
| 2013/0088221 A1 * | 4/2013 | Van Zon | B82Y 25/00 324/228 |
| 2013/0206701 A1 | 8/2013 | Strohmeier et al. | |
| 2013/0230913 A1 * | 9/2013 | Florescu | G01N 15/1436 435/288.7 |
| 2016/0209406 A1 * | 7/2016 | Aojula | B01L 3/502 |
| 2016/0363550 A1 * | 12/2016 | Koo | H04L 67/10 |
| 2017/0001197 A1 * | 1/2017 | He | G01N 33/5304 |
| 2018/0067110 A1 * | 3/2018 | Van Lieshout | G01N 33/5306 |
| 2018/0257075 A1 * | 9/2018 | Yellen | B01L 3/502761 |

OTHER PUBLICATIONS

Chinese Office Action dated Jun. 5, 2019 in a counterpart Chinese patent application No. 201710199737.4.

* cited by examiner

*Primary Examiner* — Ann Y Lam

(74) *Attorney, Agent, or Firm* — Brinks Gilson & Lione

(57) ABSTRACT

Disclosed is an analysis method including: moving a complex, by means of a magnet unit, in a flow path of a specimen cartridge which includes the flow path and a detection vessel, the complex containing a test substance formed on magnetic particles and a labeled substance binding to the test substance; taking an image of the magnetic particles in the specimen cartridge; and measuring a label of the labeled substance contained in the complex in the detection vessel.

18 Claims, 13 Drawing Sheets

ANALYSIS METHOD, ANALYZER, AND ANALYSIS SYSTEM

CROSS REFERENCE TO RELATED APPLICATIONS

This application claims priority from prior Japanese Patent Application No. 2016-109628, filed on May 31, 2016, entitled "ANALYSIS METHOD, ANALYZER, AND ANALYSIS SYSTEM", the entire content of which is incorporated herein by reference.

FIELD OF THE INVENTION

There are analyzers that perform specimen analysis by moving magnetic particles by means of a magnet (see US Patent Application Publication No. 2013/0206701, for example).

BACKGROUND

US Patent Application Publication No. 2013/0206701 mentioned above discloses an analyzer provided with a magnet unit which moves magnetic particles in a disk. The magnet unit is fixed to a cover which covers the disk. In a state where the cover is closed, magnetic particles are moved in the disk by the magnet unit.

According to US Patent Application Publication No. 2013/0206701 above, magnetic particles are moved in the disk by the magnet unit in a state where the cover is closed. Thus, the moving of the magnetic particles is difficult to be confirmed.

The present invention is directed to enabling confirmation of moving of magnetic particles while the magnetic particles are being moved by a magnet unit.

SUMMARY OF THE INVENTION

The scope of the present invention is defined solely by the appended claims, and is not affected to any degree by the statements within this summary.

An analysis method according to a first aspect of the present invention includes: moving a complex, by means of a magnet unit, in a flow path of a specimen cartridge which includes the flow path and a detection vessel, the complex containing a test substance formed on magnetic particles and a labeled substance binding to the test substance; taking an image of the magnetic particles in the specimen cartridge; and measuring a label of the labeled substance contained in the complex in the detection vessel.

An analyzer according to a second aspect of the present invention is an analyzer configured to analyze a test substance contained in a specimen by use of a specimen cartridge which includes a flow path and a detection vessel, the analyzer including: a magnet unit configured to move magnetic particles in the flow path; an imaging unit configured to take an image of the magnetic particles in the specimen cartridge; and a measurement unit configured to measure a label of a labeled substance contained in a complex, the complex containing the test substance formed on the magnetic particles in the detection vessel and the labeled substance binding to the test substance.

An analysis system according to a third aspect of the present invention includes: a specimen cartridge which includes a flow path and a detection vessel; a magnet unit configured to move magnetic particles in the flow path; an imaging unit configured to take an image of the magnetic particles in the specimen cartridge; and a measurement unit configured to measure a label of a labeled substance contained in a complex, the complex containing a test substance formed on the magnetic particles in the detection vessel and the labeled substance binding to the test substance, and the analysis system is configured to analyze the test substance contained in a specimen.

DETAILED DESCRIPTION OF THE PREFERRED EMBODIMENTS

Hereinafter, embodiments are described with reference to the drawings.

(Overview of Analyzer)

Figure 1:
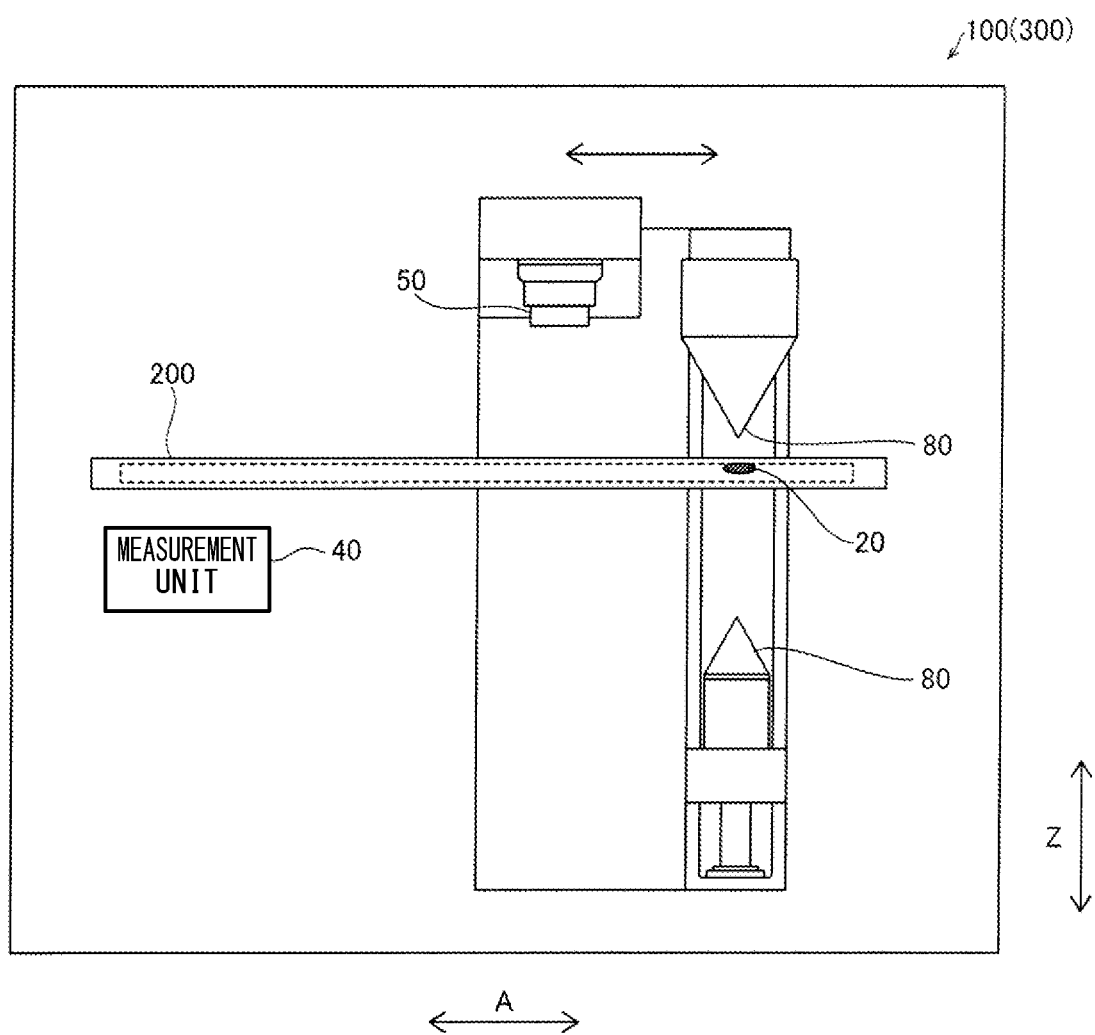
FIG. 1 is a schematic diagram of an analyzer configured to move magnetic particles by means of a magnet unit.

With reference to FIG. 1, an overview of an analyzer according to the present embodiment is described.

An analyzer 100 according to the present embodiment is configured to analyze a test substance contained in a specimen, by use of a specimen cartridge 200 provided with a flow path and a detection vessel. As shown in FIG. 1, the analyzer 100 includes a measurement unit 40, an imaging unit 50, and a magnet unit 80. An analysis system 300 is formed by the specimen cartridge 200 and the analyzer 100.

A specimen such as tissue collected from a patient, body fluid or blood collected from a patient, or the like is injected into the specimen cartridge 200. The specimen cartridge 200 into which the specimen has been injected is set to the analyzer 100. The specimen injected into the specimen cartridge 200 is analyzed through a predetermined assay, according to the functions of the specimen cartridge 200 and the functions of the analyzer 100.

In the specimen cartridge 200, the test substance and magnetic particles bind to each other to form a complex 20. The complex 20 is moved by the magnet unit 80 in the specimen cartridge 200. That is, the magnetic particles in the complex 20 are attracted by the magnetic force of the magnet unit 80. Then, the magnet unit 80 moves relative to the specimen cartridge 200, whereby the complex 20 is moved through a passage in the specimen cartridge 200.

The measurement unit 40 measures a label of a labeled substance contained in the complex 20, the complex 20 including: the test substance formed on the magnetic particles in the detection vessel and the labeled substance binding to the test substance. For example, the measurement unit 40 measures luminescence of a fluorescent substance resultant from reaction between the label contained in the complex 20 and a luminescent substrate.

The imaging unit 50 takes images of the state of the magnetic particles. The imaging unit 50 takes images of the magnetic particles being moved in the specimen cartridge 200. The imaging unit 50 takes images of the magnetic particles at least in the flow path in the specimen cartridge. The imaging unit 50 is movable relative to the specimen cartridge 200 in the horizontal direction (Direction A). That is, the imaging unit 50 is movable in the direction parallel to the direction in which the flat plate shape of the specimen cartridge 200 extends.

The magnet unit 80 moves, in the specimen cartridge 200, the complex 20 formed by the magnetic particles and the test substance being bound to each other. The magnet unit 80 is movable relative to the specimen cartridge 200, in the horizontal direction (Direction A) and in the vertical direction (Z direction). That is, the magnet unit 80 is movable in the direction parallel to and in the direction perpendicular to the direction in which the flat plate shape of the specimen cartridge 200 extends. The magnet unit 80 moves in the up-down direction (Z direction), thereby to attract the magnetic particles in the specimen cartridge 200 along the up-down direction (Z direction). The magnet unit 80 moves in the horizontal direction, thereby to move the magnetic particles in the specimen cartridge 200 along the flow path.

The imaging unit 50 moves together with the magnet unit 80 relative to the specimen cartridge 200. For example, the imaging unit 50 moves together with the magnet unit 80 relative to the specimen cartridge 200 in the horizontal direction (Direction A).

According to the configuration example shown in FIG. 1, through the movement of the magnet unit 80, the magnetic particles can be moved in the specimen cartridge 200. In addition, since images of the state of the magnetic particles in the specimen cartridge 200 can be taken by the imaging unit 50, moving of the magnetic particles can be confirmed. Accordingly, whether the magnetic particles are being normally moved in the specimen cartridge 200 can be confirmed. For example, there are cases in which: the width of the flow path in the specimen cartridge 200 is small; and where various steps such as washing, mixing of reagents, and reactions are performed in the specimen cartridge 200. Thus, when the magnetic particles are moved in order to advance reaction in the specimen cartridge 200, the magnetic particles may partially remain, in some cases. Further, in the specimen cartridge 200, measurement is performed by use of a small amount of a specimen, and thus, even a small amount of remaining magnetic particles has large influence on the measurement result. Therefore, it is important to take images to check whether or not the magnetic particles remain in the flow path in the specimen cartridge 200. In the analyzer 100 shown in FIG. 1, the state of the magnetic particles in the specimen cartridge 200 can be obtained on the basis of image data of images taken by the imaging unit 50. Thus, it is not necessary to detect the state by means of a sensor every time the magnetic particles are moved in the specimen cartridge 200. Therefore, there is no need to provide a plurality of sensors, and thus, increase in the number of components can be suppressed. In addition, the configuration of the analyzer 100 can be simplified and increase in the size of the analyzer 100 can be suppressed. Furthermore, since there is no need to perform maintenance of each of a plurality of sensors, work burden for maintenance can be reduced. Since image data of images taken by the imaging unit 50 can be obtained, the state of the magnetic particles in the specimen cartridge 200 can be confirmed, and the image data can be used in detailed analysis.

(Configuration Example of Analysis System)

Figure 2:
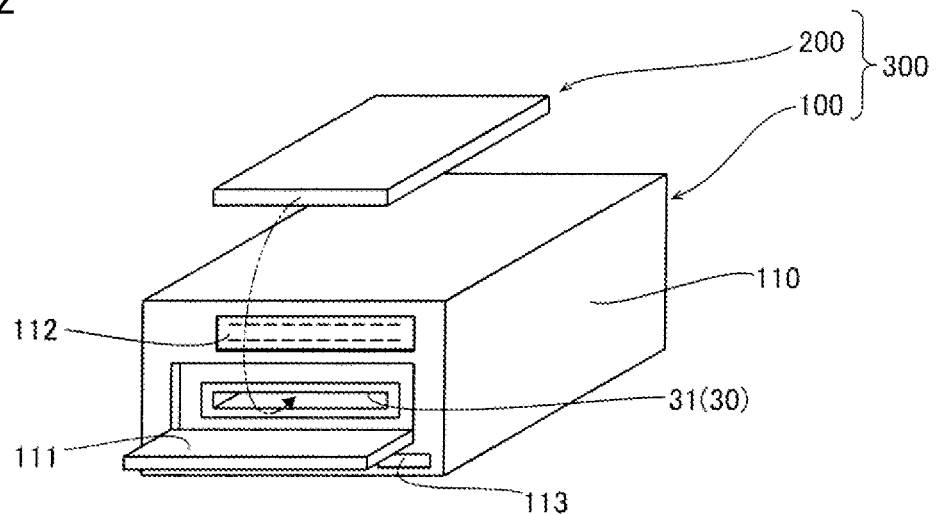
FIG. 2 is a schematic diagram showing a configuration example of the analyzer in which a specimen cartridge is used.

FIG. 2 is an external view showing one configuration example of the analyzer 100. The analyzer 100 can determine, on the basis of luminescence of the label contained in the complex 20, the presence/absence of the test substance in the specimen, and the concentration of the test substance in the specimen. The analyzer 100 is small and has a size that allows the analyzer 100 to be set on a desk in an examination room where a doctor examines a patient, for example. In FIG. 2, the size of the analyzer 100 is, for example, about 150 $cm^2$ to 300 $cm^2$ in terms of the installation area. For example, the analyzer 100 has a slot through which the specimen cartridge 200 is inserted, and the specimen cartridge 200 inserted in the slot is set at a holder 30 in the analyzer 100. The analyzer 100 performs an analysis process on the specimen cartridge 200 set at the holder 30.

In the configuration example shown in FIG. 2, the analyzer 100 includes a housing 110 for housing the apparatus body. A lateral face of the housing 110 is provided with: a lid 111 which can be opened/closed to an open position where the slot is exposed and to a close position where the slot is covered, respectively; a display part 112; and an indicator 113. The specimen cartridge 200 is inserted in the slot with the lid 111 open, and the analysis process is performed with the lid 111 closed. The display part 112 is implemented by, for example, a liquid crystal monitor or the like, and can display predetermined information such as analysis results. The indicator 113 is implemented by a lamp such as a light-emitting diode, and can indicate the state of the analyzer 100 by means of the lighting state, the color, or the like. On the display part 112, an error notification can be displayed when an error has occurred. The error may be notified through lighting/blinking of the indicator 113.

The analyzer 100 is not limited to the one as illustrated. The analyzer 100 may be configured such that: for example, a lid that can be opened/closed is provided at the upper face of the housing 110; a detection member such as the specimen cartridge 200 is set at the holder 30 in the apparatus in a state where the lid is open; and an analysis process is performed in a state where the lid is closed.

(Configuration Example of Specimen Cartridge)

Figure 3:
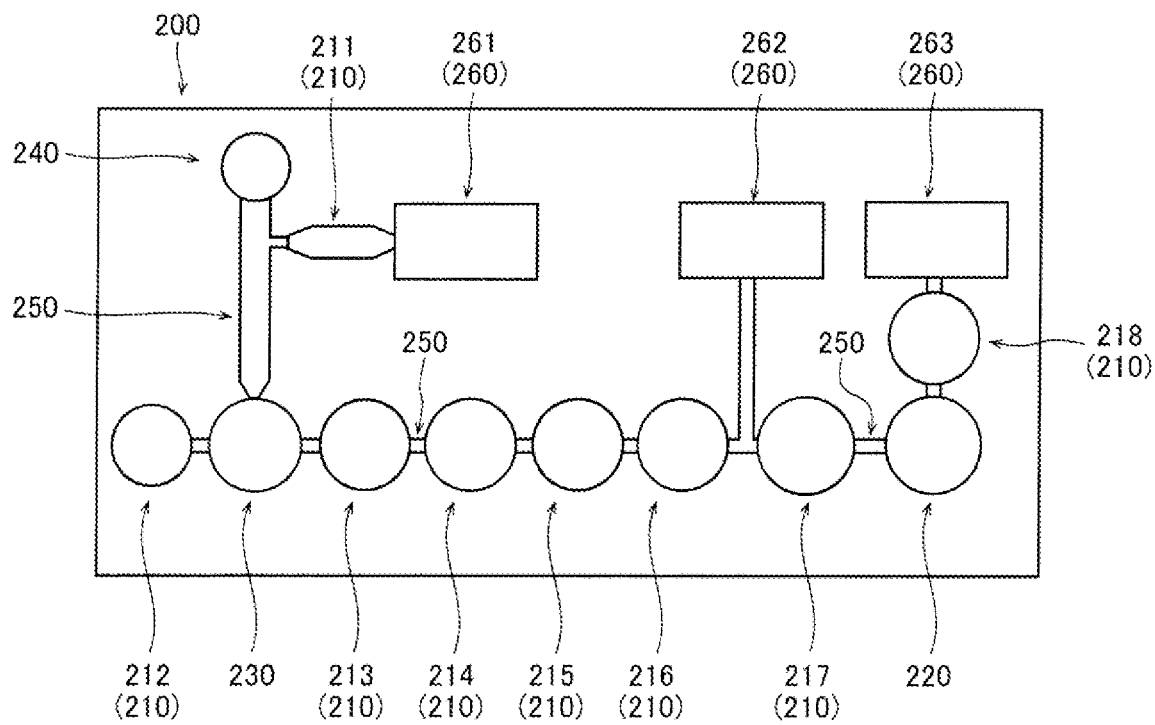
FIG. 3 is a plan view showing a configuration example of the specimen cartridge.

FIG. 3 shows a specific configuration example of the specimen cartridge 200 of the present embodiment. The specimen cartridge 200 may be a disposable cartridge. In that case, the specimen cartridge 200 is stored in a state of being kept in a package, and is used after being taken out of the package. The specimen cartridge 200 is formed in a flat plate shape.

The specimen cartridge 200 has a plurality of liquid storage portions 210 each for storing a liquid such as a specimen, a reagent, or a washing liquid. Here, an example in which the specimen is blood is shown. Some of the reagents include magnetic particles which react with a substance containing a test substance. The specimen cartridge 200 has a detection vessel 220 and a liquid reaction portion 230. The specimen cartridge 200 includes a passage through which the complex 20 is moved that is formed by the magnetic particles and the test substance being bound to each other. The specimen cartridge 200 is formed from a transparent or translucent material. Thus, images of the magnetic particles being moved in the specimen cartridge 200 can be taken by the imaging unit 50.

The specimen is injected into a hemocyte separator 240 of the specimen cartridge 200. The specimen cartridge 200 with the hemocyte separator 240 sealed is inserted into the analyzer 100. The hemocyte separator 240 separates hemocyte components from the injected blood.

In the configuration example shown in FIG. 3, the liquid storage portions 210 include eight liquid storage portions 211, 212, 213, 214, 215, 216, 217, and 218. The liquid storage portions 211 to 218, the detection vessel 220, the liquid reaction portion 230, and the hemocyte separator 240 are arranged in the order according to process steps, and are connected via a passage portion 250 along the transfer route for liquid or the magnetic particles.

The specimen cartridge 200 has an air chamber 260. In the configuration example shown in FIG. 3, three air chambers 260, i.e., air chambers, 261, 262, and 263, are provided. Air sent out from the air chambers 260 causes a portion of the liquid in the specimen cartridge 200 to be transferred.

(Configuration Example of Analyzer)

Figure 4:
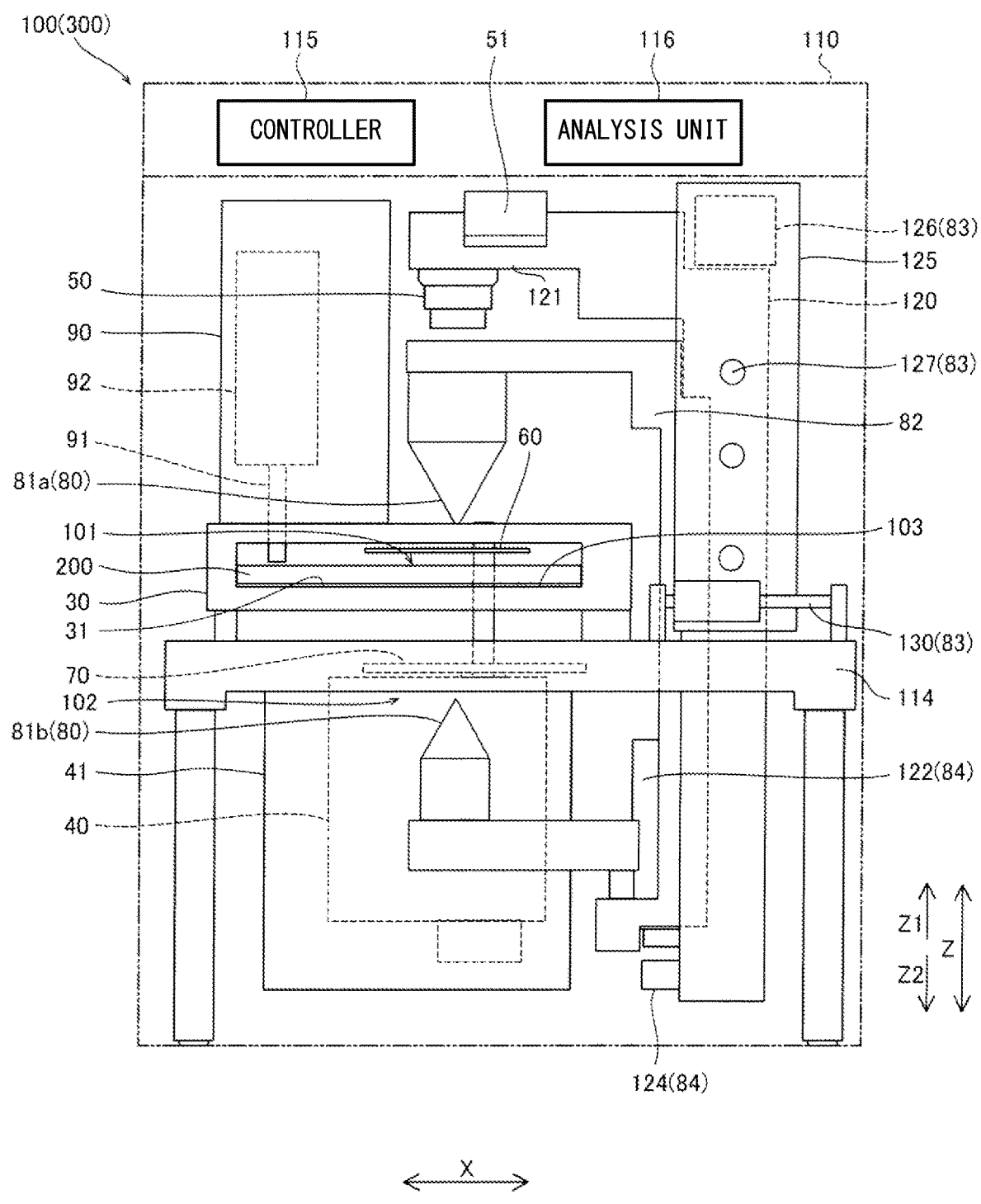
FIG. 4 is an internal front view showing the configuration example of the analyzer.
Figure 5:
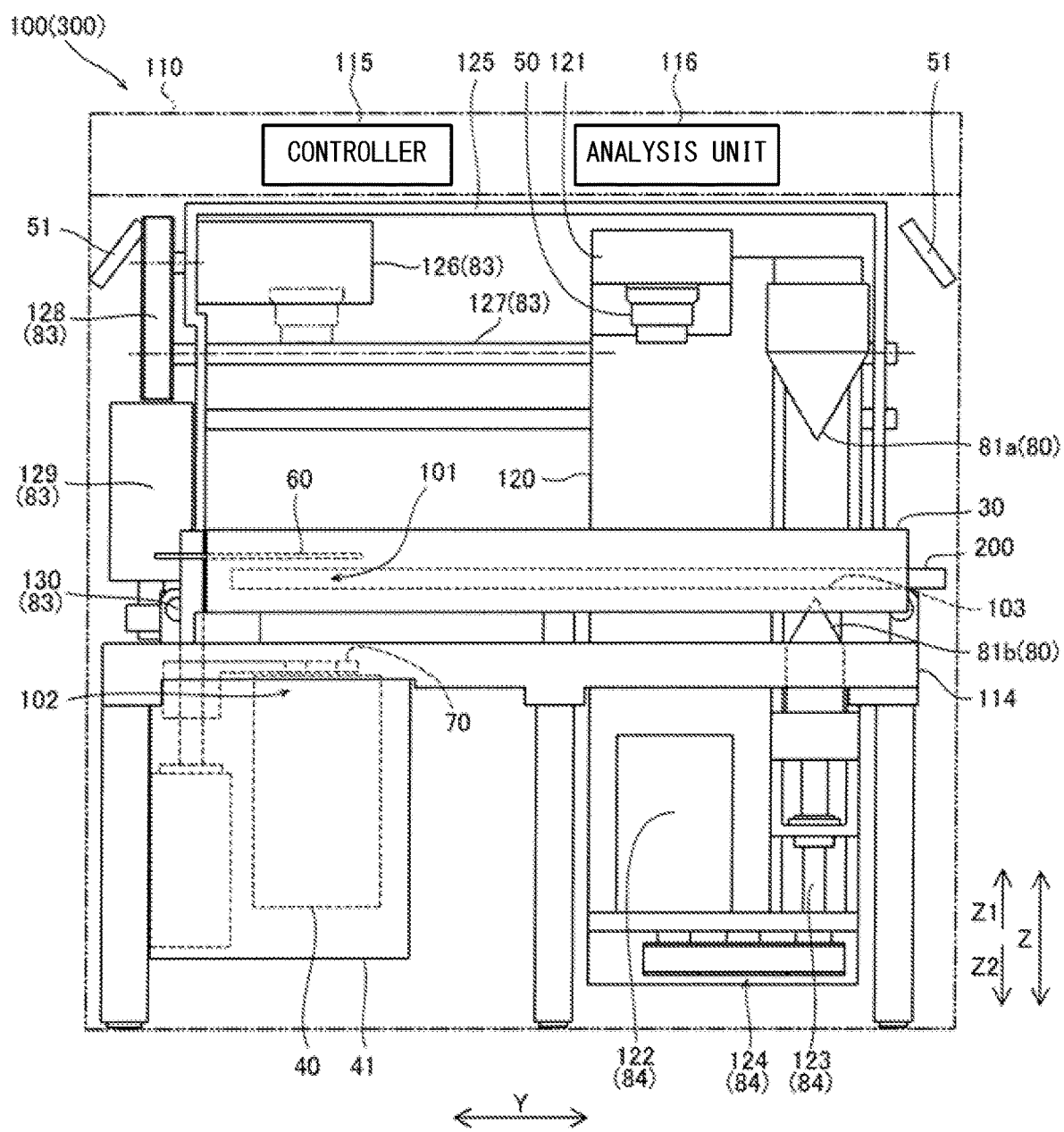
FIG. 5 is an internal side view showing the configuration example of the analyzer.
Figure 6:
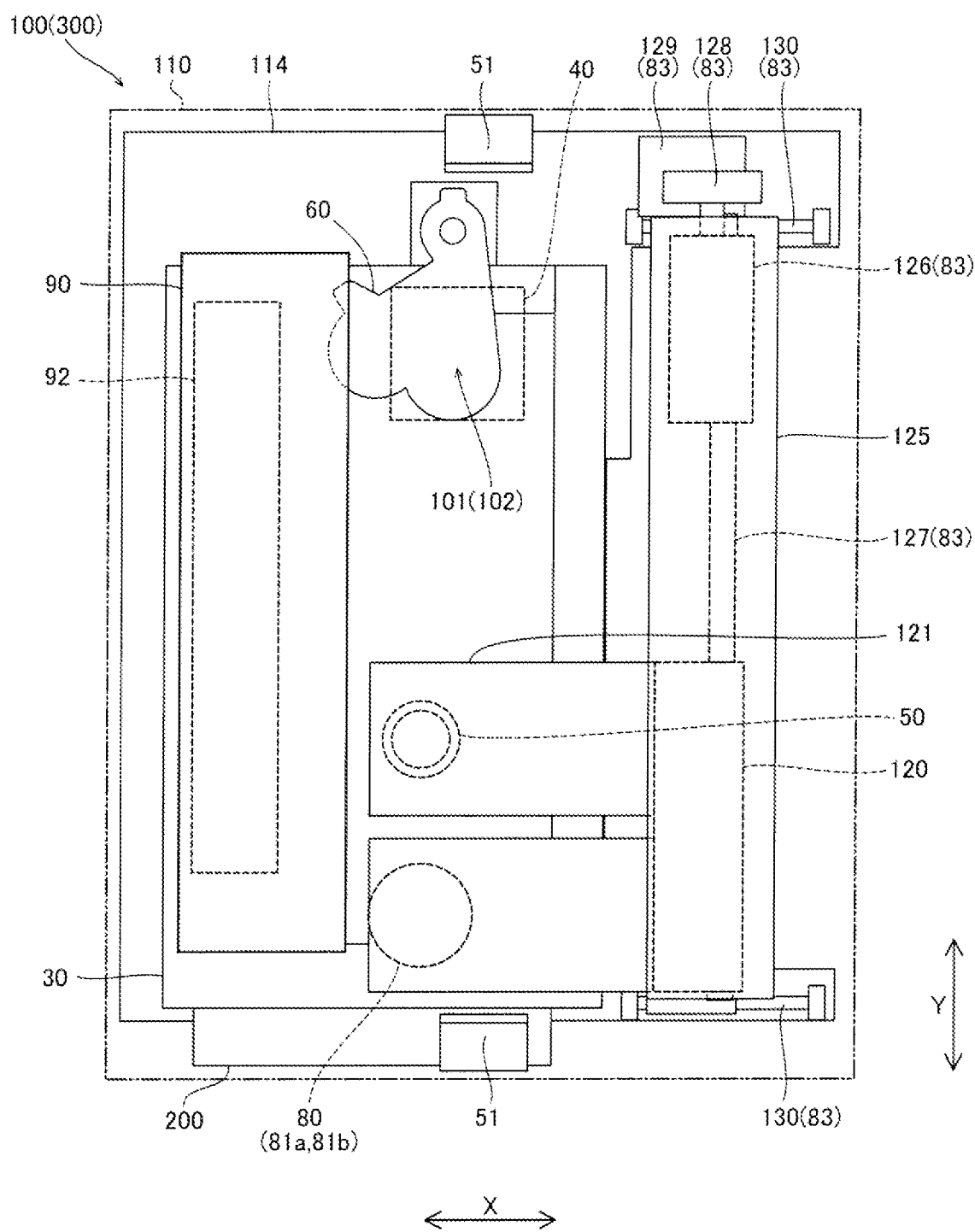
FIG. 6 is an internal plan view showing the configuration example of the analyzer.

FIG. 4 to FIG. 6 show a specific configuration example of the analyzer 100 in which the specimen cartridge 200 is used.

The analyzer 100 includes the holder 30, the measurement unit 40, the imaging unit 50, a reflector 60, and the magnet unit 80. The holder 30, the measurement unit 40, the imaging unit 50, the reflector 60, and the magnet unit 80 are housed in the housing 110. In the configuration example shown in FIG. 4 to FIG. 6, the analyzer 100 further includes a plunger unit 90.

The holder 30 holds, at a predetermined position, the specimen cartridge 200 inserted through an opening 31 (see FIG. 4) which is a slot portion of the analyzer 100. The holder 30 holds the specimen cartridge 200 in a state where the specimen cartridge 200 is substantially parallel to the installation face of the analyzer 100. Since the installation face of the analyzer 100 can be regarded as being substantially horizontal, the face or the direction that is parallel to the installation face of the analyzer 100 is herein referred to as the horizontal plane or the horizontal direction. In the description below, for convenience, the short-side direction of the analyzer 100 in the horizontal plane is defined as X direction, and the longitudinal direction of the analyzer 100 in the horizontal plane is defined as Y direction. The up-down direction orthogonal to the X direction and the Y direction is defined as Z direction.

In the configuration example shown in FIG. 4 to FIG. 6, the holder 30 detachably holds the specimen cartridge 200, into which a specimen is injected, whereby the specimen and reagents are mixed together therein, whereby a complex 20 is prepared therein. The holder 30 is configured to dispose, at a measurement position 101, the detection vessel 220 (see FIG. 3) of the specimen cartridge 200. Thus, the analyzer 100 can perform preparation of the complex 20 and detection of light on the basis of the label contained in the complex 20, in a state where the specimen cartridge 200 having the specimen injected therein is set at the holder 30. Thus, there is no need to prepare the complex 20 in advance, and thus, convenience for the user is enhanced.

The holder 30 is set on a base 114 and can support the periphery of the specimen cartridge 200. In order to allow taking images and light detection, the holder 30 is formed so as to partially expose the upper face side and the lower face side of the specimen cartridge 200. The holder 30 may have any structure as long as the holder 30 can hold the specimen cartridge 200.

The measurement unit 40 measures a signal based on the label contained in the complex 20 at the measurement position 101 in the specimen cartridge 200. Specifically, the measurement unit 40 measures luminescence of the label contained in the complex 20. For example, the measurement unit 40 is implemented by a known light sensor. The light sensor is, for example, a photomultiplier, a phototube, a photodiode, or the like. The measurement unit 40 is fixedly disposed at light-receiving position 102 below the measurement position 101. The measurement unit 40 has the light-receiving position 102 at the upper face side which is the measurement position 101 side. The measurement unit 40 detects, through an opening formed at the lower face side of the holder 30, light that has reached from the measurement position 101 to the light-receiving position 102. The measurement unit 40 is housed in a case 41, and is light-shielded except the light-receiving position 102.

In the configuration example shown in FIG. 4 to FIG. 6, the reflector 60 is a mirror member disposed at an upper position relative to the measurement position 101 and to the side opposite to the measurement unit 40. The reflector 60 moves relative to the measurement unit 40, the specimen cartridge 200, and the imaging unit 50. The reflector 60 is configured to enter a reflecting state, between the measurement position 101 and the imaging unit 50, and at a reflecting position which is opposed to the measurement unit 40 with the measurement position 101 interposed between the measurement unit 40 and the reflector 60. In addition, the reflector 60 is configured to enter an open state at a withdrawn position at which the reflector 60 does not block the space between the measurement position 101 and the imaging unit 50.

In the configuration example shown in FIG. 4 to FIG. 6, the analyzer 100 further includes a light adjuster 70 (see FIG. 4 and FIG. 5) disposed between the measurement position 101 and the measurement unit 40. Light adjuster 70 is configured to be switchable between: a light transmitting state in which light advancing from the measurement position 101 toward the measurement unit 40 is allowed to be transmitted therethrough; and a light blocking state in which light advancing from the measurement position 101 toward the measurement unit 40 is blocked. Accordingly, when light from the complex 20 is to be detected, light detection can be performed by setting the light adjuster 70 to the light transmitting state, and other than when the detection is performed, light toward the measurement unit 40 can be blocked by setting the light adjuster 70 to the light blocking state as necessary. Thus, unnecessary light from the outside can be suppressed from being incident on the measurement unit 40, and thus, the detection sensitivity of the measurement unit 40 can be further enhanced.

The imaging unit 50 takes images of the state of the magnetic particles. Specifically, the imaging unit 50 takes images of the magnetic particles being moved in the specimen cartridge 200. Thus, the moving of the magnetic particles can be confirmed. Furthermore, the imaging unit 50 takes images of moving of the liquid in the flow path in the specimen cartridge 200, and a bubble mixture state. The imaging unit 50 is implemented by a known small-sized camera, for example. The small-sized camera includes, for example, a CCD image sensor, a CMOS image sensor, or the like. The imaging unit 50 has a view angle of about 100 degrees to 130 degrees, for example. The imaging unit 50 has an imaging range having a radius of about 20 mm to 50 mm, for example. The imaging unit 50 can take a moving image or a still image. The imaging unit 50 has a field of view that allows taking images of a portion of the specimen cartridge 200. Thus, a detailed moving image or a detailed still image of a region that includes the magnetic particles can be obtained. The imaging unit 50 is disposed above the measurement position 101. As shown in FIG. 4, the imaging unit 50 is provided at a position above the holder 30 such that the image taking direction thereof extends downward. The imaging unit 50 is configured to be movable in the X direction and in the Y direction. It should be noted that a background part 103 having a color distinguishable from the magnetic particles may be disposed to the side opposite to the imaging unit 50 relative to the specimen cartridge 200. The background part 103 may be provided to the specimen cartridge 200, or may be provided to the holder 30 of the analyzer 100. This allows the imaging unit 50 to take clearer images of the magnetic particles. In a case where the magnetic particles are brown, the color of the background part 103 is preferred to be white, gray, or black in this order.

The imaging unit 50 moves together with the magnet unit 80 relative to the specimen cartridge 200. This can suppress occurrence of a dead angle that is caused by movement of the magnet unit 80 in a case where the imaging unit 50 is fixed. In addition, an image of the magnetic particles being moved by the magnet unit 80 can be taken by the imaging unit 50, along the direction in which the magnet unit 80 moves. The imaging unit 50 moves together with the magnet unit 80 relative to the specimen cartridge 200, in the directions (XY directions) parallel to the direction in which the flat plate shape of the specimen cartridge 200 extends. Accordingly, moving of the imaging unit 50 and moving in the horizontal direction of the magnet unit 80 can be realized by a common movement mechanism. Thus, increase in the number of components can be suppressed, and the movement mechanism for the imaging unit 50 and the magnet unit 80 can be simplified.

In order to allow taking images, the analyzer 100 includes a lighting unit 51. The lighting unit 51 is implemented by, for example, a light-emitting diode or the like. A pair of the lighting units 51 is provided, for example, above the holder 30 and near both ends in the Y direction of the holder 30. Each lighting unit 51 is disposed near the center in the X direction, for example. Accordingly, the imaging field of the imaging unit 50 is illuminated by the illuminating light from both sides in the Y direction.

In the configuration example shown in FIG. 4 to FIG. 6, the magnet unit 80 moves, in the specimen cartridge 200, the complex 20 formed by the magnetic particles and the test substance being bound to each other. As the magnet unit 80, a pair of magnet units 81a and 81b are provided so as to sandwich the specimen cartridge 200. One magnet unit 81a is disposed above (Z1 side) the specimen cartridge 200 and the holder 30, and the other magnet unit 81b is disposed below (Z2 side) the specimen cartridge 200 and the holder 30. The magnet units 80 are supported by a connecting portion 82. Specifically, the pair of the magnet units 81a and 81b are held, with a predetermined interval in the up-down direction therebetween, by the connecting portion 82. As shown in FIG. 5, the magnet unit 80 can move in each of the X direction, the Y direction, and the Z direction. The imaging unit 50 can move integrally with the magnet unit 81a in the X direction and in the Y direction. In a range excluding the periphery of the measurement position 101, the imaging unit 50 can move integrally with the magnet unit 81b in the X direction and the Y direction. In the periphery of the measurement position 101, the magnet unit 81b comes into contact with the case 41 of the measurement unit 40, whereby the moving of magnet unit 81b is restricted. When the moving of the magnet unit 81b is restricted, the magnet unit 81b is rotated about a predetermined rotation axis, and does not advance any further in the measurement position 101 direction. The magnet units 81a and 81b can move independently of the imaging unit 50 in the Z direction. The imaging unit 50 does not move in the Z direction.

The magnet units 81a and 81b each have a tapered shape, and the tip thereof serves as a magnetizing portion. As a result of downward movement of the magnet unit 81a, the magnet unit 81a approaches the upper face of the specimen cartridge 200, whereby the magnet unit 81a causes magnetic force to act on the specimen cartridge 200 from above. As a result of upward movement of the magnet unit 81b, the magnet unit 81b approaches the lower face of the specimen cartridge 200, whereby the magnet unit 81b causes magnetic force to act on the specimen cartridge 200 from below. In the holder 30, the upper face side and the lower face side of the specimen cartridge 200 are exposed at least in the range in which the magnet units 81a and 81b move.

The magnetic particles are collected in the specimen cartridge 200 by causing the magnet unit 81a or 81b to approach the specimen cartridge 200. The collected magnetic particles are moved in the horizontal direction by causing the magnet unit 81a or 81b located close to the specimen cartridge 200 to move in the horizontal direction. The magnetic particles in the specimen cartridge 200 can be moved in the up-down direction by causing the magnet units 81a and 81b to reciprocate in the up-down direction such that the magnet units 81a and 81b alternately approach the specimen cartridge 200. As a result, the magnetic particles and the liquid in the specimen cartridge 200 are agitated.

As shown in FIG. 4, the plunger unit 90 is disposed at the upper face side of the holder 30. The plunger unit 90 includes a plunger 91 and a drive unit 92 which operates the plunger 91. The plunger 91 is disposed above the air chambers 260 (see FIG. 4) of the specimen cartridge 200 held by the holder 30, and can move in the up-down direction. The plunger 91 is provided by the same number as the air chambers 260, for example, and the drive unit 92 causes the respective plungers 91 to move in the up-down direction independently of or in conjunction with one another. The plunger unit 90 pushes down the air chambers 260 of the specimen cartridge 200 by means of the plungers 91. Pushing down of the plungers 91 causes air to be sent out of the air chambers 260, whereby part or all of the liquid in the specimen cartridge 200 is transferred. In the holder 30, the upper face side and the lower face side of the specimen cartridge 200 are exposed at least in the range in which the magnet units 81a and 81b move.

The analyzer 100 includes a controller 115 for controlling the apparatus, and an analysis unit 116 which analyzes an output signal from the measurement unit 40. The controller 115 controls the measurement unit 40, the imaging unit 50, and the reflector 60, thereby controlling image taking operation and light detecting operation. The analysis unit 116 performs analysis on the basis of the amount of light detected by the measurement unit 40. The analyzer 100 may output the detection result of the measurement unit 40 to a computer separately provided, for example, and may perform analysis by use of the computer.

The controller 115 includes, for example, an arithmetic processor and a storage unit. The arithmetic processor is implemented by, for example, a CPU (central processing unit), an MPU (micro processing unit), or the like. The storage unit is implemented by, for example, a flash memory, a hard disk memory, or the like. In the storage unit, thresholds to be used in abnormality detection, timings at which images whose abnormality was detected were obtained, and the like are stored. In the storage unit, the distance between the magnet unit 80 and the imaging unit 50 is stored. The controller 115 obtains the state of the magnetic particles in the specimen cartridge 200 on the basis of image data of an image taken by the imaging unit 50. Thus, since the state of the magnetic particles in the specimen cartridge 200 can be easily obtained by the controller 115, occurrence of an error can be quickly notified to a user in the middle of measurement. The image data includes RGB pixel value information of each pixel of the image taken by the imaging unit 50. The controller 115 detects the magnetic particles on the basis of color information or contrast information of the image data of the image taken by the imaging unit 50. Therefore, the magnetic particles can be easily recognized from the taken image on the basis of the color information or the contrast information.

On the basis of the image data of the image taken by the imaging unit 50, the controller 115 detects the flow path, and detects the magnetic particles in the detected flow path. The flow path is a passage through which the fluid in the specimen cartridge 200 passes, and includes the liquid storage portions 211 to 218, the detection vessel 220, the liquid reaction portion 230, the hemocyte separator 240, and the passage portion 250. Since whether the presence or absence of the magnetic particles outside the flow path in the image data is not analyzed, it is possible to suppress occurrence of erroneous detection in which the magnetic particles outside the flow path are detected. As a result, the magnetic particles can be accurately detected.

On the basis of the image data of the image taken by the imaging unit 50, the controller 115 obtains, as the state of the magnetic particles in the specimen cartridge 200, whether the magnetic particles remain by not less than a predetermined amount at a place that is away from the magnet unit 80 by not less than a predetermined distance, or whether the magnetic particles are normally agitated. For example, on the basis of the distance between the imaging unit 50 and the magnet unit 80 stored in the storage unit, the controller 115 specifies the position of the magnet unit 80 in the image data, and obtains the distance between the magnetic particles and the magnet unit 80, on the basis of the specified position of the magnet unit 80 and the position of the magnetic particles in the image data. Alternatively, the controller 115 obtains the distance between the magnetic particles and the magnet unit 80 on the basis of the position of the magnet unit 80 in the image data and the position of the magnetic particles in the image data. The position of the magnet unit 80 may be the position of the tip of the magnet unit 80. This makes it possible to perform the measurement work while detecting, in the middle of the measurement, the remaining state of the magnetic particles and the agitation state of the magnetic particles. Therefore, for example, in a case where the state of moving of the magnetic particles, the remaining state of the magnetic particles, the agitation state of the magnetic particles, and the like are not appropriate, it is possible to suppress occurrence of measurement failure by redoing the operation. Furthermore, for example, when an error has been detected, it is also possible to suspend the measurement work in the middle of the measurement.

On the basis of the image data of the image of the detection vessel 220 taken by the imaging unit 50, the controller 115 obtains, as the state of the magnetic particles in the specimen cartridge 200, whether the magnetic particles forming the complex 20 are normally being moved to the detection vessel 220. Accordingly, whether the complex 20 has been normally moved to the measurement position 101 can be determined, and thus, the complex 20 can be accurately measured.

The controller 115 obtains the amount of the magnetic particles in the detection vessel 220, from the image data of the image of the detection vessel 220 taken by the imaging unit 50, and corrects the measurement result from the measurement unit 40, on the basis of the obtained amount of the magnetic particles. Accordingly, the concentration of the complex 20 can be accurately obtained on the basis of both of the measurement performed by the measurement unit 40 and the amount of the magnetic particles obtained from the image taken by the imaging unit 50.

On the basis of change in the amount of the magnetic particles in the image data of the image taken by the imaging unit 50, the controller 115 obtains whether the magnetic particles are normally agitated by the magnet unit 80. Thus, whether the agitation state is good can be determined in the middle of the measurement.

On the basis of the image data of the image taken by the imaging unit 50, the controller 115 measures, as the state of the magnetic particles in the specimen cartridge 200, the amount of the magnetic particles at a distance shorter than or equal to a predetermined distance from the magnet unit 80, and obtains whether the magnetic particles are normally being moved. That is, the controller 115 measures increase/decrease in the amount of the magnetic particles moved by the magnet unit 80, and obtains the state of moving of the magnetic particles.

On the basis of the image data of the image taken by the imaging unit 50, the controller 115 detects mixture of a bubble into the detection vessel 220 or into the flow path of the specimen cartridge 200. Thus, occurrence of mixture of a bubble into the flow path can be determined in the middle of the measurement.

On the basis of the obtained state of the magnetic particles in the specimen cartridge 200, the controller 115 makes notification of an error. Thus, occurrence of the error can be quickly notified to the user in the middle of the measurement. For example, in a case where the magnetic particles in the specimen cartridge 200 remain by not less than a predetermined amount at a place that is away from the magnet unit 80 by not less than a predetermined distance, the controller 115 performs control of displaying an error notification on the display part 112 so as to indicate that an error has occurred. When the magnetic particles in the specimen cartridge 200 are not normally being agitated, the controller 115 performs control of displaying an error notification on the display part 112 so as to indicate that an error has occurred. When the magnetic particles forming the complex 20 are not normally being moved to the detection vessel 220, the controller 115 performs control of displaying an error notification on the display part 112 so as to indicate that an error has occurred. When a bubble has been mixed in the detection vessel 220 or in the flow path of the specimen cartridge 200, the controller 115 performs control of displaying an error notification on the display part 112 so as to indicate that an error has occurred. Other than being displayed on the display part 112, the error notification may be notified by sound, or may be notified both by sound and by being displayed. The error notification may be notified by use of an external monitor, or the like.

The controller 115 may be provided outside the analyzer 100. For example, the controller 115 may be implemented by a computer connected to the analyzer 100.

(Movement Mechanism for Imaging Unit and Magnet Unit)

A movement mechanism for the imaging unit 50 and the magnet unit 80 in the configuration example shown in FIG. 4 to FIG. 6 is described. In the configuration example shown in FIG. 4 to FIG. 6, the analyzer 100 further includes a first movement mechanism unit 83 which moves both the imaging unit 50 and the magnet unit 80 in the horizontal direction (XY directions). The analyzer 100 further includes a second movement mechanism unit 84 which moves the magnet unit 80 in the vertical direction (Z direction). As shown in FIG. 5, the imaging unit 50 is fixed to a support portion 120. Specifically, the imaging unit 50 is mounted to a leading end portion of an arm 121 (see FIG. 4) extending in the X direction from an upper portion of the support portion 120. The magnet unit 80 is mounted so as to be movable in the up-down direction relative to the support portion 120. That is, the support portion 120 supports both the magnet unit 80 and the imaging unit 50 so as to be able to perform relative movement in directions parallel to the flat-plate-shaped specimen cartridge 200 (XY directions). Thus, both the magnet unit 80 and the imaging unit 50 can be easily moved in the horizontal direction. The support portion 120 is provided, as the second movement mechanism unit 84, with a Z-axis motor 122 and a transmission mechanism. In the configuration example shown in FIG. 5, the transmission mechanism is configured by a combination of: a feed-screw mechanism 123 extending in the Z direction and for moving the magnet unit 80; and a belt pulley mechanism 124 which transmits driving force of the Z-axis motor 122 to the feed-screw mechanism 123. Through rotation of the Z-axis motor 122, the magnet unit 80 moves in the Z direction relative to the support portion 120.

The support portion 120 is supported by a movable body 125 so as to be movable in the Y direction. The movable body 125 is provided, as the first movement mechanism unit 83, with a Y-axis motor 126 and a transmission mechanism. In the configuration example shown in FIG. 5, the transmission mechanism is configured by a combination of: a feed-screw mechanism 127 extending in the Y direction and for moving the support portion 120; and a belt pulley mechanism 128 which transmits driving force of the Y-axis motor 126 to the feed-screw mechanism 127. Through rotation of the Y-axis motor 126, the support portion 120 which supports the imaging unit 50 and the magnet unit 80 moves in the Y direction relative to the movable body 125.

The movable body 125 is supported by the base 114 so as to be movable in the X direction. As the first movement mechanism unit 83, an X-axis motor 129, a guide shaft 130 (see FIG. 6), and a transmission mechanism not shown are provided on the base 114. The guide shaft 130 guides movement in the X direction of the movable body 125. Through rotation of the X-axis motor 129, the movable body 125, and the support portion 120 which supports the imaging unit 50 and the magnet unit 80 move in the X direction relative to the base 114. The configurations of the transmission mechanisms and the motors are not limited to those shown.

In the configuration example shown in FIG. 4 to FIG. 6, the imaging unit 50 and the magnet unit 80 move, thereby realizing relative movement of the imaging unit 50 and the magnet unit 80 relative to the specimen cartridge 200. Other than the configuration in which the imaging unit 50 and the magnet unit 80 move, a configuration may be employed in which: the specimen cartridge 200 moves, thereby realizing relative movement the imaging unit 50 and the magnet unit 80 relative to the specimen cartridge 200. Alternatively, a configuration may be employed in which: both of the imaging unit 50 and the magnet unit 80, and the specimen cartridge 200 move, thereby realizing relative movement of the imaging unit 50 and the magnet unit 80 relative to the specimen cartridge 200.

(Description of Operation of Analyzer)

Figure 7:
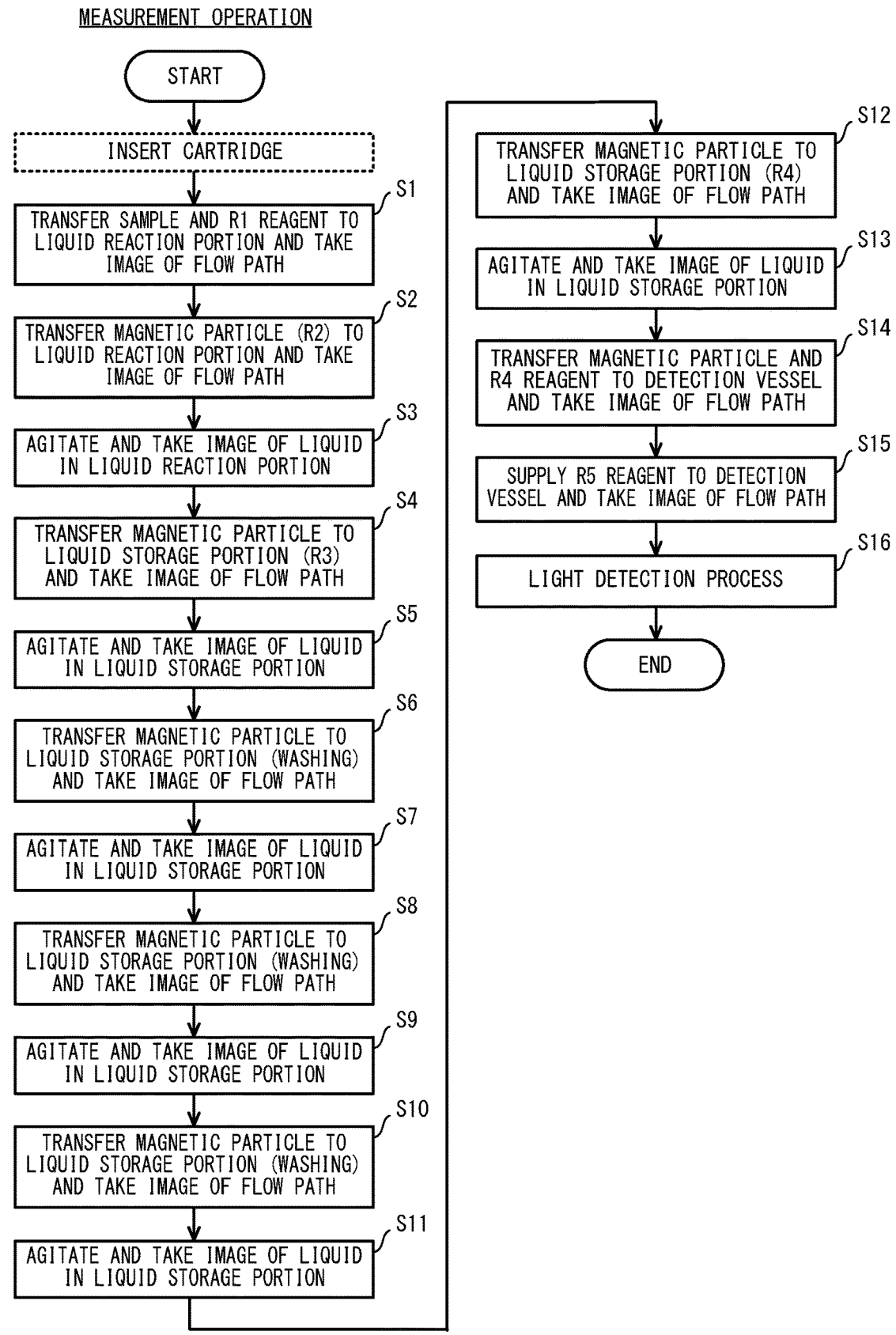
FIG. 7 is a flow chart for explaining measurement operation performed by the analyzer.

FIG. 7 shows an example of operation performed when a predetermined assay is conducted by use of the analyzer 100 and the specimen cartridge 200 of the present embodiment. In the description of the operation, as to the configuration of the specimen cartridge 200, FIG. 3 is referred to. As to the configuration of the analyzer 100, FIG. 4 to FIG. 6 are referred to. Control of the components of the analyzer 100 is performed by the controller 115.

First, a user inserts the specimen cartridge 200 into the slot of the analyzer 100. The specimen cartridge 200 is taken out of a package, and a specimen collected from a patient is injected into the specimen cartridge 200. Then, the specimen cartridge 200 is inserted into the slot of the analyzer 100, thereby to be held by the holder 30. The test substance in the specimen contains an antigen, for example. One example of the antigen is Hepatitis B surface antigen (HBsAg). The test substance may be one or more of antigens, antibodies, and other proteins.

When the specimen cartridge 200 is set at the holder 30, taking images of the specimen cartridge 200 by the imaging unit 50 is enabled. The controller 115 turns on the lighting units 51 and causes the imaging unit 50 to take images of phases of the measurement operation in the form of a moving image. Still images may be taken by the imaging unit 50.

In step S1, the specimen is sent to the liquid reaction portion 230. The controller 115 controls the plunger unit 90 to push down the air chamber 261. The air sent out from the air chamber 261 causes the specimen to flow through the passage portion 250 together with an R1 reagent stored in the liquid storage portion 211, to be pushed into the liquid reaction portion 230. At this time, the imaging unit 50 takes an image of the flow path that includes the liquid reaction portion 230 and the passage portion 250. On the basis of the taken image, the controller 115 determines whether the specimen and the R1 reagent have reached the liquid reaction portion 230. In addition, the controller 115 determines whether a bubble has been mixed in the flow path. Specifically, the controller 115 determines whether a bubble has been mixed, through a bubble detection process described later with reference to FIG. 12.

The R1 reagent contains a capture substance that binds to the test substance. The capture substance contains an antibody that binds to the test substance, for example. The antibody is a biotin-bound HBs monoclonal antibody, for example. The test substance and the R1 reagent bind to each other through antigen-antibody reaction.

In step S2, the analyzer 100 transfers, to the liquid reaction portion 230, the magnetic particles contained in a R2 reagent stored in the liquid storage portion 212. The magnetic particles are dispersed in the liquid component of the R2 reagent. The controller 115 causes the magnet unit 80 to move, thereby to collect the magnetic particles in the liquid storage portion 212 by the magnetic force and move the collected magnetic particles to the liquid reaction portion 230. At this time, the imaging unit 50 takes an image of the flow path that includes the liquid storage portion 212 and the liquid reaction portion 230. On the basis of the taken image, the controller 115 determines whether the magnetic particles have reached the liquid reaction portion 230. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through a process of detecting the remaining state of the magnetic particles described later with reference to FIG. 13.

In step S3, the analyzer 100 agitates the liquid in the liquid reaction portion 230. Specifically, the magnet unit 80 is cyclically caused to move in the up-down direction, thereby moving the magnetic particles within the liquid reaction portion 230. As a result, the liquid in the liquid reaction portion 230 is agitated. For example, the agitation is performed in a cycle of about two seconds about 200 times to 300 times. That is, the magnet unit 80 reciprocates in the up-down direction, in a cycle of about two seconds about 200 times to 300 times. At this time, the imaging unit 50 takes an image of the liquid reaction portion 230. On the basis of the taken image, the controller 115 determines whether the agitation has been normally performed. Specifically, the controller 115 determines whether the agitation has been normally performed, through a process of quantitative determination of magnetic particle agitation efficiency described later with reference to FIG. 16. In addition, the controller 115 determines whether a bubble has been mixed in the liquid reaction portion 230. Specifically, the controller 115 determines whether a bubble has been mixed, through the bubble detection process described later with reference to FIG. 12.

In the liquid reaction portion 230, a magnetic-particle-bound body is generated through reaction between the magnetic particles and an antigen-antibody reaction product. That is, the test substance bound to the capture substance of the R1 reagent binds to the magnetic particles via the capture substance. The magnetic particles serve as the carrier for the test substance. The magnetic particles are, for example, streptavidin-bound the magnetic particles, the surfaces of which are coated with avidin.

In step S4, the analyzer 100 transfers, by the magnetic force of the magnet unit 80, the magnetic-particle-bound body to the liquid storage portion 213 storing an R3 reagent therein. At this time, the imaging unit 50 takes an image of the flow path that includes the liquid reaction portion 230 and the liquid storage portion 213. On the basis of the taken image, the controller 115 determines whether the magnetic-particle-bound body has reached the liquid storage portion 213. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

In step S5, the analyzer 100 agitates the liquid in the liquid storage portion 213. Specifically, the magnet unit 80 is cyclically caused to move in the up-down direction, thereby moving the magnetic particles within the liquid storage portion 213. As a result, the liquid in the liquid storage portion 213 is agitated. For example, the agitation is performed in a cycle of about two seconds about 200 times to 300 times. That is, the magnet unit 80 reciprocates in the up-down direction in a cycle of about two seconds about 200 times to 300 times. At this time, the imaging unit 50 takes an image of the liquid storage portion 213. On the basis of the taken image, the controller 115 determines whether the agitation has been normally performed. Specifically, the controller 115 determines whether the agitation has been normally performed, through the process of quantitative determination of magnetic particle agitation efficiency described later with reference to FIG. 16. In addition, the controller 115 determines whether a bubble has been mixed in the liquid storage portion 213. Specifically, the controller 115 determines whether a bubble has been mixed, through the bubble detection process described later with reference to FIG. 12.

The R3 reagent contains the labeled substance. The labeled antibody contained in the R3 reagent and the magnetic-particle-bound body are allowed to react with each other. An immune complex is generated through reaction between the magnetic-particle-bound body and the labeled antibody. The immune complex contains the test substance, the capture antibody, the labeled antibody, and the magnetic particles.

In step S6, the analyzer 100 transfers, to the liquid storage portion 214, the immune complex by the magnetic force of the magnet unit 80. The liquid storage portion 214 stores a washing liquid therein. In the liquid storage portion 214, the immune complex and unreacted substances are separated from each other. That is, unreacted substances are removed through washing. At this time, the imaging unit 50 takes an image of the flow path that includes the liquid storage portion 213 and the liquid storage portion 214. On the basis of the taken image, the controller 115 determines whether the magnetic-particle-bound body has reached the liquid storage portion 214. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

In step S7, the analyzer 100 agitates the liquid in the liquid storage portion 214. Specifically, the magnet unit 80 is cyclically caused to move in the up-down direction, thereby moving the magnetic particles within the liquid storage portion 214. As a result, the liquid in the liquid storage portion 214 is agitated. For example, the agitation is performed in a cycle of about two seconds about 200 times to 300 times. That is, the magnet unit 80 reciprocates in the up-down direction in a cycle of about two seconds about 200 times to 300 times. At this time, the imaging unit 50 takes an image of the liquid storage portion 214. On the basis of the taken image, the controller 115 determines whether the agitation has been normally performed. Specifically, the controller 115 determines whether the agitation has been normally performed, through the process of quantitative determination of magnetic particle agitation efficiency described later with reference to FIG. 16. In addition, the controller 115 determines whether a bubble has been mixed in the liquid storage portion 214. Specifically, the controller 115 determines whether a bubble has been mixed, through the bubble detection process described later with reference to FIG. 12.

In step S8, the analyzer 100 transfers, to the liquid storage portion 215, the immune complex by the magnetic force of the magnet unit 80. The liquid storage portion 215 stores a washing liquid therein. In the liquid storage portion 215, the immune complex and unreacted substances are separated from each other. That is, unreacted substances are removed through washing. At this time, the imaging unit 50 takes an image of the flow path that includes the liquid storage portion 214 and the liquid storage portion 215. On the basis of the taken image, the controller 115 determines whether the magnetic-particle-bound body has reached the liquid storage portion 215. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

In step S9, the analyzer 100 agitates the liquid in the liquid storage portion 215. Specifically, the magnet unit 80 is cyclically caused to move in the up-down direction, thereby moving the magnetic particles within the liquid storage portion 215. As a result, the liquid in the liquid storage portion 215 is agitated. For example, the agitation is performed in a cycle of about two seconds about 200 times to 300 times. That is, the magnet unit 80 reciprocates in the up-down direction in a cycle of about two seconds about 200 times to 300 times. At this time, the imaging unit 50 takes an image of the liquid storage portion 215. On the basis of the taken image, the controller 115 determines whether the agitation has been normally performed. Specifically, the controller 115 determines whether the agitation has been normally performed, through the process of quantitative determination of magnetic particle agitation efficiency described later with reference to FIG. 16. In addition, the controller 115 determines whether a bubble has been mixed in the liquid storage portion 215. Specifically, the controller 115 determines whether a bubble has been mixed, through the bubble detection process described later with reference to FIG. 12.

In step S10, the analyzer 100 transfers, to the liquid storage portion 216, the immune complex by the magnetic force of the magnet unit 80. The liquid storage portion 216 stores a washing liquid therein. In the liquid storage portion 216, the immune complex and unreacted substances are separated from each other. That is, unreacted substances are removed through washing. At this time, the imaging unit 50 takes an image of the flow path that includes the liquid storage portion 215 and the liquid storage portion 216. On the basis of the taken image, the controller 115 determines whether the magnetic-particle-bound body has reached the liquid storage portion 216. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

In step S11, the analyzer 100 agitates the liquid in the liquid storage portion 216. Specifically, the magnet unit 80 is cyclically caused to move in the up-down direction, thereby moving the magnetic particles within the liquid storage portion 216. As a result, the liquid in the liquid storage portion 216 is agitated. For example, the agitation is performed in a cycle of about two seconds about 200 times to 300 times. That is, the magnet unit 80 reciprocates in the up-down direction in a cycle of about two seconds about 200 times to 300 times. At this time, the imaging unit 50 takes an image of the liquid storage portion 216. On the basis of the taken image, the controller 115 determines whether the agitation has been normally performed. Specifically, the controller 115 determines whether the agitation has been normally performed, through the process of quantitative determination of magnetic particle agitation efficiency described later with reference to FIG. 16. In addition, the controller 115 determines whether a bubble has been mixed in the liquid storage portion 216. Specifically, the controller 115 determines whether a bubble has been mixed, through the bubble detection process described later with reference to FIG. 12.

In step S12, the analyzer 100 transfers, to the liquid storage portion 217, the immune complex by the magnetic force of the magnet unit 80. At this time, the imaging unit 50 takes an image of the flow path that includes the liquid storage portion 216 and the liquid storage portion 217. On the basis of the taken image, the controller 115 determines whether the magnetic-particle-bound body has reached the liquid storage portion 217. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

The liquid storage portion 217 stores an R4 reagent therein. The R4 reagent has a composition that promotes luminescence of the immune complex. The R4 reagent is a buffer solution, for example. The immune complex reacts, in the liquid storage portion 217, with the buffer solution contained in the R4 reagent.

In step S13, the analyzer 100 agitates the liquid in the liquid storage portion 217. Specifically, the magnet unit 80 is cyclically caused to move in the up-down direction, thereby moving the magnetic particles within the liquid storage portion 217. As a result, the liquid in the liquid storage portion 217 is agitated. For example, the agitation is performed in a cycle of about two seconds about 200 times to 300 times. That is, the magnet unit 80 reciprocates in the up-down direction in a cycle of about two seconds about 200 times to 300 times. At this time, the imaging unit 50 takes an image of the liquid storage portion 217. On the basis of the taken image, the controller 115 determines whether the agitation has been normally performed. Specifically, the controller 115 determines whether the agitation has been normally performed, through the process of quantitative determination of magnetic particle agitation efficiency described later with reference to FIG. 16. In addition, the controller 115 determines whether a bubble has been mixed in the liquid storage portion 217. Specifically, the controller 115 determines whether a bubble has been mixed, through the bubble detection process described later with reference to FIG. 12.

In step S14, the analyzer 100 transfers, to the detection vessel 220, the mixture of the immune complex and the buffer solution. The controller 115 controls the plunger unit 90 to push down the air chamber 262, thereby to push out the mixture of the immune complex and the buffer solution via the passage portion 250 to the detection vessel 220. The immune complex may be transferred to the detection vessel 220 also by the magnetic force of the magnet unit 80. At this time, the imaging unit 50 takes an image of the flow path that includes the liquid storage portion 217 and the detection vessel 220. On the basis of the taken image, the controller 115 determines whether the magnetic-particle-bound body has reached the detection vessel 220. In addition, the controller 115 determines whether the magnetic particles remain in the flow path, and whether a bubble has been mixed in the flow path. Specifically, the controller 115 determines whether a bubble has been mixed, through the bubble detection process described later with reference to FIG. 12. In addition, the controller 115 determines whether the magnetic particles remain in the flow path, through the process of detecting the remaining state of the magnetic particles described later with reference to FIG. 13.

In step S15, the analyzer 100 transfers, to the detection vessel 220, an R5 reagent stored in the liquid storage portion 218. The controller 115 controls the plunger unit 90 to push down the air chamber 263, thereby to push out the R5 reagent from the liquid storage portion 218 to the detection vessel 220. At this time, the imaging unit 50 takes an image of the flow path that includes the liquid storage portion 218 and the detection vessel 220. On the basis of the taken image, the controller 115 determines whether a bubble has been mixed in the flow path. Specifically, the controller 115 determines whether a bubble has been mixed, through the bubble detection process described later with reference to FIG. 12. In addition, on the basis of the taken image, the controller 115 determines whether the R5 reagent has reached the detection vessel 220.

The R5 reagent contains, for example, a substrate that reacts with the immune complex to promote luminescence. The R5 reagent is added to the mixture of the immune complex and the buffer solution in the detection vessel 220. The luminescent substrate and the immune complex react with each other. As a result, a luminescent sample that generates light is prepared in the detection vessel 220.

The controller 115 causes the imaging unit 50 to take an image of the detection vessel 220 located at the measurement position 101. On the basis of the taken image of the luminescent sample, the controller 115 controls the light detecting operation that uses the measurement unit 40. Thus, whether the luminescent sample is present at the measurement position 101, and whether the state of the luminescent sample is appropriate can be determined on the basis of the taken image. As a result, in such a case where the state of the luminescent sample in the specimen cartridge 200 is not appropriate, it is possible to stop the process without performing the light detecting operation, to quickly notify the user, and to correct the analysis result depending on the state of the luminescent sample. In addition, the controller 115 determines whether a bubble has been mixed in the detection vessel 220.

When the state of the luminescent sample in the taken image is appropriate, the controller 115 performs the subsequent detection processing operation. For example, when the luminescent sample is not shown in the taken image, it is conceivable that the liquid has not reached the detection vessel 220. Thus, the controller 115 does not perform the subsequent detection processing operation, but displays an error on the display part 112 and on the indicator 113. For example, when the state of the luminescent sample in the taken image is not appropriate, the controller 115 performs the subsequent detection processing operation but displays, on the display part 112, an indication of a possible error together with the analysis result.

In step S16, the analyzer 100 performs the light detection process. Specifically, the measurement unit 40 detects the light generated through reaction between the luminescent substrate and the labeled antibody of the immune complex. Then, the measurement operation is ended.

As the magnetic particles, any particles may be used that contain, as the base material, a material having magnetic properties, and that can be used in ordinary immunoassay. For example, the magnetic particles using, as the base material, $Fe_2O_3$ and/or $Fe_3O_4$, cobalt, nickel, ferrite, magnetite, or the like can be used. The magnetic particles may be coated with a binding substance for binding the magnetic particles to the test substance. Alternatively, the magnetic particles may be bound to the test substance via a capture substance for binding the magnetic particles to the test substance. The capture substance is an antigen, an antibody, or the like that mutually binds to the magnetic particles and the test substance.

The labeled substance binds to the test substance through antigen-antibody reaction, and contains a label that can be measured by the measurement unit 40. The labeled substance is not limited to a particular one as long as the labeled substance is an antibody that contains a known label that is used in immunoassay. When a capture substance is used, the labeled substance may bind to the capture substance. Examples of the label contained in the labeled substance include enzyme, fluorescent substance, radioisotope, and the like. Examples of the enzyme include alkaline phosphatase (ALP), peroxidase, glucose oxidase, tyrosinase, acid phosphatase, and the like. As the fluorescent substance, fluorescein isothiocyanate (FITC), green fluorescent protein (GFP), luciferin, or the like can be used. As the radioisotope, 125I, 14C, 32P, or the like can be used.

When the label is an enzyme, a substrate for the enzyme of the labeled substance may be selected from known substrates as appropriate in accordance with the enzyme that is used. When the enzyme is alkaline phosphatase, examples of the substrate include: chemiluminescent substrates such as CDP-Star (registered-trademark), (disodium 4-chloro-3-(methoxyspiro[1,2-dioxetane-3,2'-(5'-chloro)tricyclo [3.3.1.13,7]decane]-4-yl)phenylphosphate), and CSPD (registered-trademark) (disodium 3-(4-methoxyspiro[1,2-dioxetane-3,2-(5'-chloro)tricyclo[3.3.1.13,7]decane]-4-yl) phenylphosphate); luminescent substrates such as p-nitrophenyl phosphate, 5-bromo-4-chloro-3-indolyl phosphate (BCIP), 4-nitroblue tetrazolium chloride (NBT), and iodonitrotetrazolium (INT); fluorescent substrates such as 4-methylumbelliferyl phosphate (4MUP); chromogenic substrates such as 5-bromo-4-chloro-3-indolyl phosphate (BCIP), disodium 5-bromo-6-chloro-indolyl phosphate, and p-nitrophenyl phosphate; and the like.

(Description of Magnetic Particle Detection Method)

A method for detecting the magnetic particles on the basis of image data of an image taken by the imaging unit 50 is described.

Now, an example case is described in which: for the purpose of detecting the magnetic particles, performed are detection of whether the magnetic particles remain in each liquid storage portion where washing is performed, and detection of abnormality in the shape of the liquid in an upper portion of the liquid storage portion where washing is performed. In the detection of the magnetic particles, abnormality is detected by analytically determining a magnetic particle region on the basis of a taken image.

Figure 8:
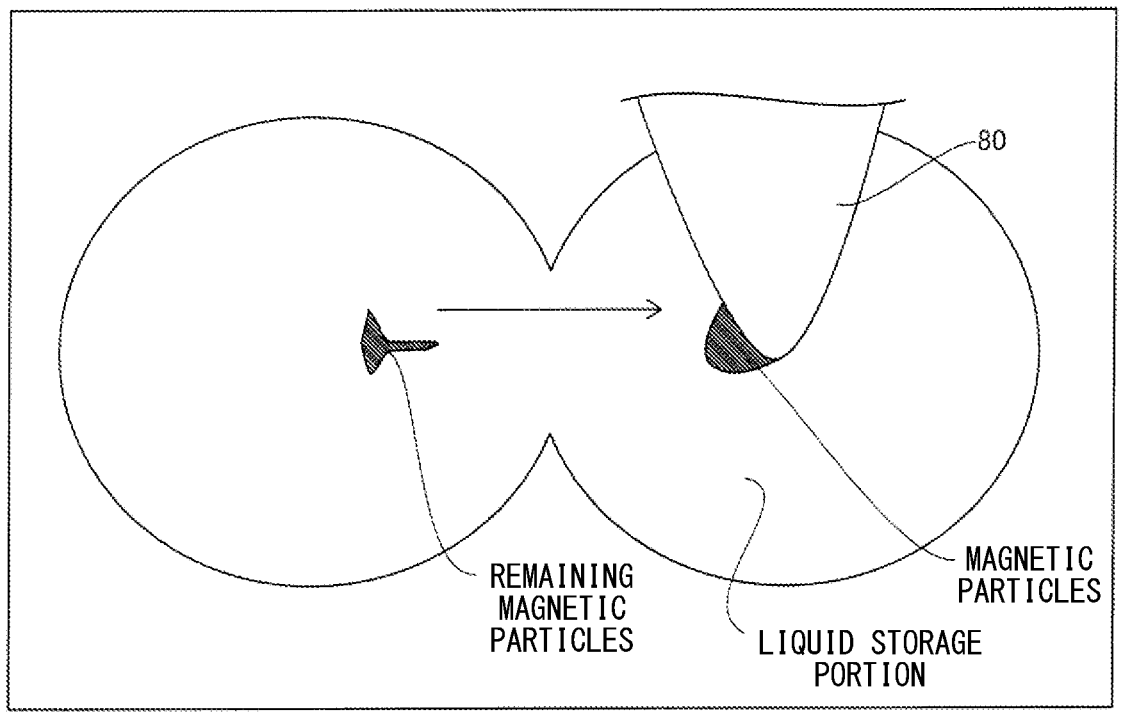
FIG. 8 is an example of an image showing the magnetic particles that remain.
Figure 9:
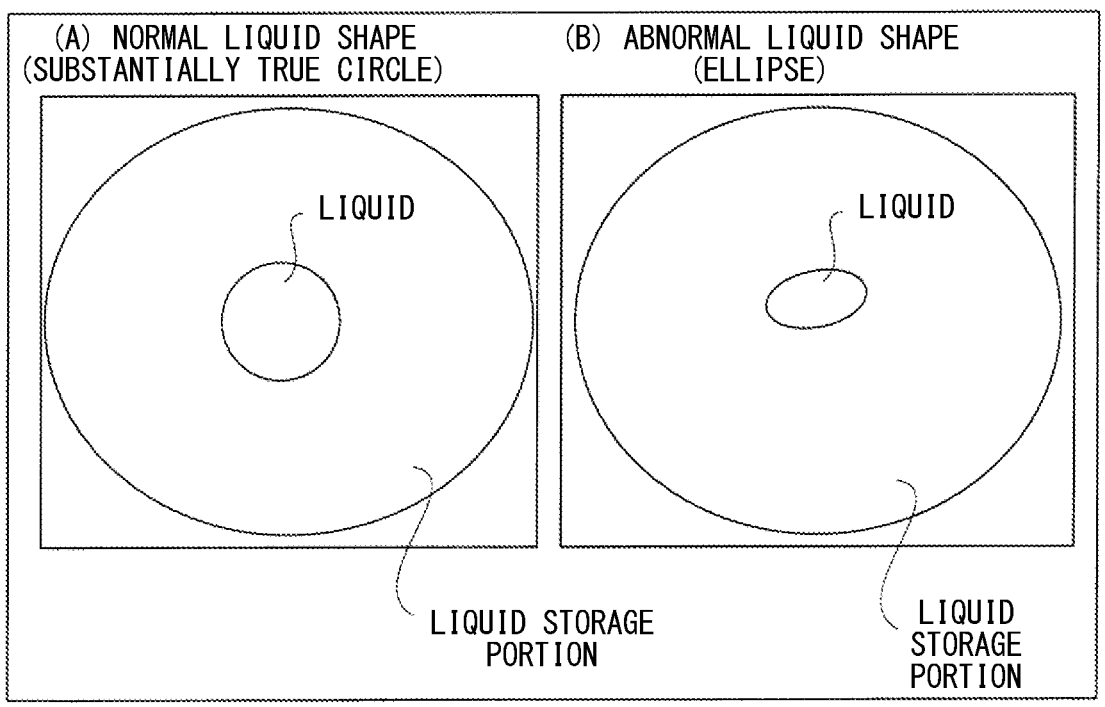
FIG. 9 is an example of images of liquid in a liquid storage portion.

Regarding the detection of whether the magnetic particles remain in a liquid storage portion where washing is performed, if the magnetic particles remain in the liquid storage portion where washing is performed as shown in FIG. 8, there are magnetic particles that do not reach the detection vessel, and this causes a lowered measurement value. Regarding the detection of abnormality in the shape of the liquid in an upper portion of the liquid storage portion where washing is performed, if the shape of the liquid formed in an upper portion of the liquid storage portion where washing is performed is a substantially true circle as shown in (A) of FIG. 9, this shape is the normal shape of the liquid in the upper portion of the liquid storage portion, and represents a state where the washing is sufficiently performed. Meanwhile, if the shape of the liquid formed in an upper portion of the liquid storage portion where washing is performed is not a true circle but is an ellipse as shown in (B) of FIG. 9, this shape is an abnormal shape of the liquid in the upper portion of the liquid storage portion, and represents a state where the washing is not sufficiently performed.

In a case where whether the magnetic particles remain in the liquid storage portion where washing is performed is detected, a magnetic particle region is obtained in the liquid storage portion where washing has been completed or on the route through which the magnetic particles have already been moved. Then, the place where the magnetic particles remain and the amount of the remaining magnetic particles are estimated. Thereby, whether magnetic particle remaining state abnormality has occurred is determined.

In a case where abnormality in the shape of the liquid in an upper portion of the liquid storage portion where washing is performed is detected, while the magnetic particles being washed are attracted to an upper portion of the liquid storage portion, whether the shape of the liquid in the upper portion of the liquid storage portion is normal is determined on the basis of the area of the magnetic particle region.

For the detection of the magnetic particle region, color information is used. The color of the magnetic particle region changes in accordance with the amount of the magnetic particles. Thus, in a region where the amount of the magnetic particles is large, the color of the magnetic particles themselves is dominant, and in a region where the amount of the magnetic particles is small, scattered/reflected light from the periphery is dominant. In addition, since the color changes in accordance with the amount of very fine magnetic particles present in a certain space, it is assumed that the change in color is caused by intermediate color mixing. Therefore, change in color relative to the amount of the magnetic particles can be perceived in the HSL color space. The HSL color space is a space that represents color in terms of hue H, saturation S, and lightness L.

Figure 10:
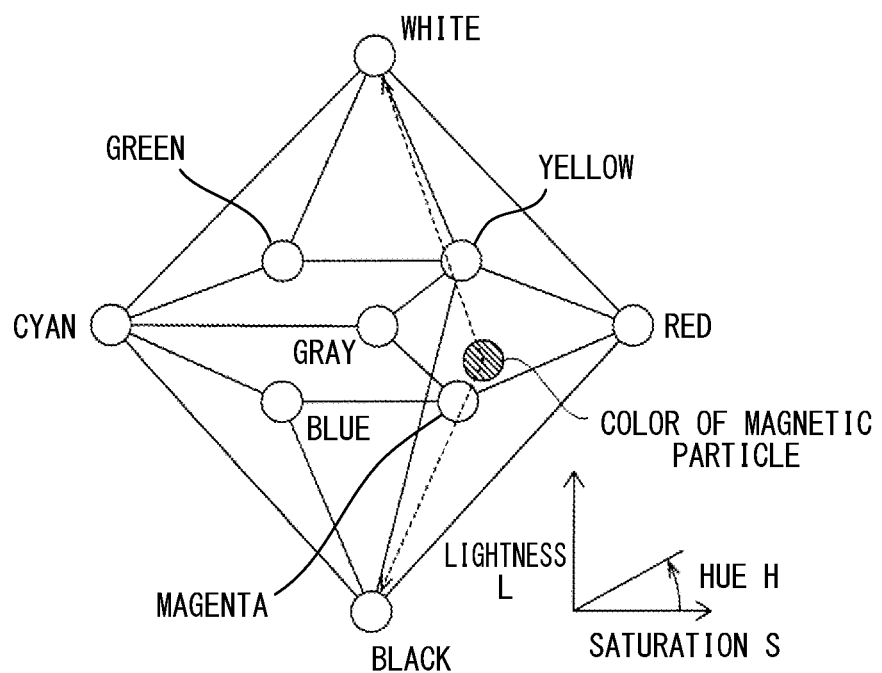
FIG. 10 is a diagram for explaining an HSL color space.

Here, as shown in FIG. 10, it is assumed that the intermediate color mixing is realized by the component of the background color (for example, white or black) and the component of the color of magnetic particle. As the amount of the magnetic particles decreases, the color linearly approaches the background color (white or black) accordingly, staring at the color of magnetic particle in the HSL color space. This relationship is used as a color model.

By use of the color model of the magnetic particle, whether the magnetic particles are present is determined, for each pixel in the taken image. Color change due to the intermediate color mixing of the color of magnetic particle and the background color (white or black) is on a straight line connecting two colors that are mixed in the HSL color space. Thus, on this straight line, the hue H does not change. In addition, as the color approaches white, the lightness L linearly increases accordingly. Meanwhile, as the color approaches black, the lightness L linearly decreases accordingly. Here, in order to find a region where the magnetic particles are present, the hue H is used which does not change due to color mixing of white and black. An RGB value is read from the analysis target pixel and is converted into an HSL value. If the obtained hue H is similar to the hue H of the magnetic particle, it is determined that the magnetic particles are present at the analysis target pixel.

Figure 11:
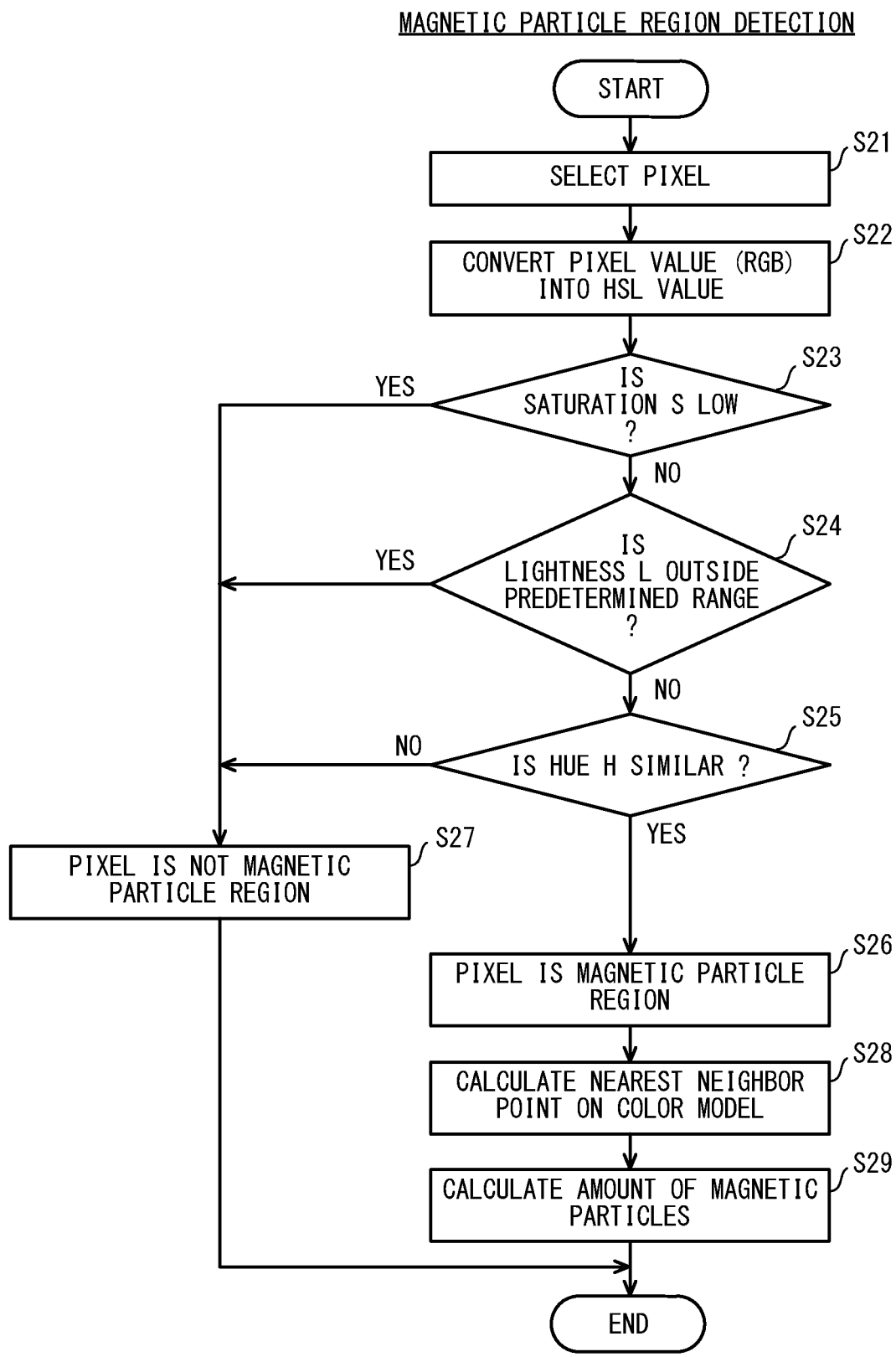
FIG. 11 is a flow chart for explaining a process of magnetic particle region detection performed by the analyzer.

A procedure of magnetic particle region detection is described with reference to FIG. 11.

In step S21, the controller 115 selects an analysis target pixel from a taken image. In step S22, the controller 115 converts the pixel value (RGB) of the selected pixel into an HSL value. In step S23, on the basis of the saturation S of the color of magnetic particle, the controller 115 determines whether the saturation S of the selected pixel is lower than a predetermined value. When the saturation S of the selected pixel is lower than the predetermined value, the process is advanced to step S27. When the saturation S of the selected pixel is not lower than the predetermined value, the process is advanced to step S24. When the saturation S of the selected pixel is low, the calculation error of the hue H becomes large, and it becomes difficult to perform determination of the magnetic particle region by use of the hue H. Thus, when the saturation S of the selected pixel is low, the determination is performed assuming that the magnetic particle is not present.

In step S24, the controller 115 determines whether the lightness L of the selected pixel is outside a predetermined range. When the lightness L of the selected pixel is outside the predetermined range, the process is advanced to step S27. When the lightness L of the selected pixel is inside the predetermined range, the process is advanced to step S25. When the lightness L of the selected pixel is lower or higher than the predetermined range and outside the predetermined range, the calculation errors of the saturation S and of the hue H of the selected pixel become large, and thus, it becomes difficult to perform determination of the magnetic particle region by use of the hue H. Thus, when the lightness L of the selected pixel is outside the predetermined range, the determination is performed assuming that the magnetic particle is not present.

In step S25, the controller 115 determines whether the hue H of the selected pixel is similar to the hue H of the magnetic particle. When the hue H of the selected pixel is not similar to the hue H of the magnetic particle, the process is advanced to step S27. When the hue H of the selected pixel is similar to the hue H of the magnetic particle, the process is advanced to step S26. In step S26, the controller 115 determines that the selected pixel is the magnetic particle region. Meanwhile, when the process is advanced to step S27, it is determined that the selected pixel is not the magnetic particle region.

In step S28, the controller 115 calculates a nearest neighbor point on the color model. Specifically, with the dimension of the hue H excluded, a nearest neighbor point is calculated by use of an orthogonal coordinate space of the saturation S and the lightness L. A straight line is obtained that connects the color of the magnetic particle which is the color model of the magnetic particle and white or black which is the background color. Then, the point at which the distance in the orthogonal coordinate system from the lightness L and the saturation S of the selected pixel to the obtained straight line becomes minimum is obtained. The obtained point is considered as the color of the magnetic particle region estimated from the color model. Here, the saturation S does not change in the color model, and thus, the estimated result of the saturation S is constant regardless of the actually measured saturation S. Thus, the estimated result of the lightness L has the same value as that of the actually measured lightness L.

In step S29, the controller 115 calculates the amount of the magnetic particles. Since the lightness L increases or decreases associated with the amount of the magnetic particles, the amount of the magnetic particles is estimated from the lightness L. It is assumed that the relationship between the lightness L and the amount of the magnetic particles is nonlinear. Then, the process regarding the selected pixel ends, and then, the next pixel is selected. With respect to each of all the necessary pixels on the image, after whether the pixel is of the magnetic particles is determined, and the amount of the magnetic particles is calculated in a case where the pixel is of the magnetic particles, the detection of the magnetic particle region is ended.

From the detected magnetic particles on the image, whether the magnetic particles remain is detected. Specifically, if the magnetic particles have been detected in the image of the liquid storage portion where washing is performed, the fact that the magnetic particles remain is detected, and the amount of the remaining magnetic particles is calculated from the region of the remaining magnetic particles and from the amount of the magnetic particles. If the magnetic particles remain by an amount that could be problematic in terms of measurement, this is determined as magnetic particle remaining state abnormality.

From the detected magnetic particles on the image, the shape of the liquid in an upper portion in the liquid storage portion where washing is performed is detected. Specifically, an image is obtained at the time point when the magnetic particles are concentrated at an upper portion of the liquid in an upper portion of the liquid storage portion, and the magnetic particle region is detected. Accordingly, the shape of the liquid in the upper portion of the liquid storage portion can be clearly detected. Thus, detection of abnormality in the liquid in the upper portion of the liquid storage portion can be reliably performed. Determination of a true circle is performed by obtaining the area of the magnetic particle region.

(Description of Bubble Detection Method)

Figure 12:
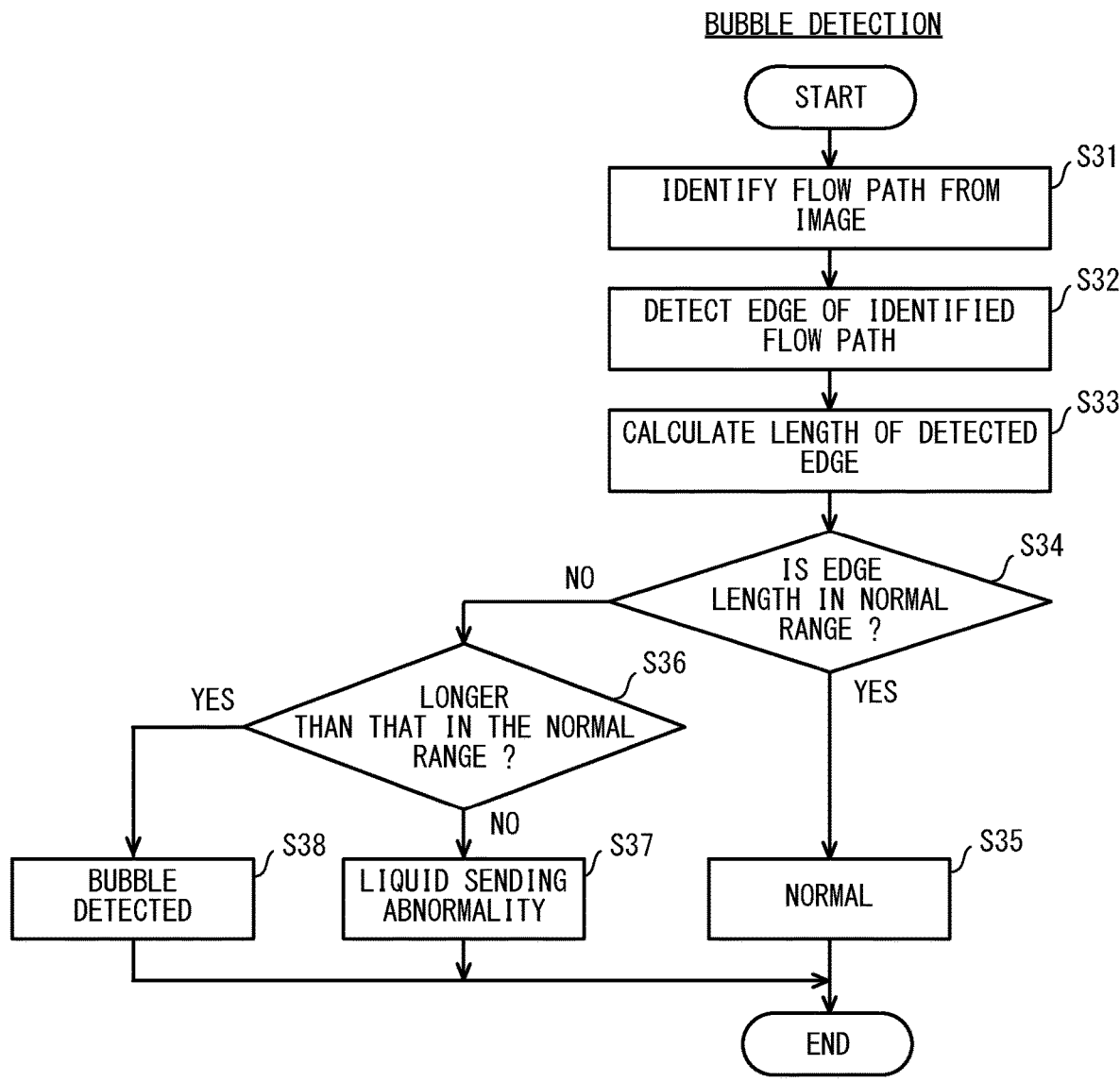
FIG. 12 is a flow chart for explaining a process of detecting a bubble in the flow path of the analyzer.

With reference to FIG. 12, a process of detecting bubbles in the flow path is described.

In step S31, the controller 115 identifies the flow path in an image taken by the imaging unit 50. Specifically, on the basis of the position of the imaging unit 50 and information of the flow path of the specimen cartridge 200, the controller 115 identifies the flow path in the image. In step S32, the controller 115 detects the edge of the identified flow path. Specifically, the controller 115 detects a portion having a changed pixel value in the flow path of the taken image.

In step S33, the controller 115 calculates the length of the edge of the detected flow path. Specifically, the controller 115 calculates the number of pixels in the image that have been identified as the edge, to calculate the length of the edge.

In step S34, the controller 115 determines whether the length of the edge of the flow path is within a normal range. When the length of the edge is within the normal range, the process is advanced to step S35, and when the length of the edge is outside the normal range, the process is advanced to step S36. In step S35, the controller 115 determines that no bubble has been mixed in the flow path and that the state is normal. The normal range is set on the basis of the length of the border between the flow path and the fluid. That is, since an edge is formed between the flow path and the fluid, if no bubble has been mixed, the edge is detected that corresponds to the length of the border between the flow path and the fluid.

In step S36, the controller 115 determines whether the edge length is longer than the normal range. When the edge length is shorter than the normal range, the process is advanced to step S37, and when the edge length is longer than the normal range, the process is advanced to step S38. In step S38, the controller 115 determines that a bubble has been mixed in the flow path. That is, when an edge exists other than between the flow path and the fluid, the edge length is extended compared to that in the normal range. The edge that corresponds to the extended portion is the border between the liquid layer and the gas layer in the flow path.

In step S37, the controller 115 determines that the state corresponds to a liquid sending abnormality in which the liquid is not flowing in the flow path. That is, when the liquid is not being sent, the edge of the border of the flow path and the fluid is shortened by the reduced amount of the fluid.

(Description of Method for Detecting Remaining State of Magnetic Particles)

Figure 13:
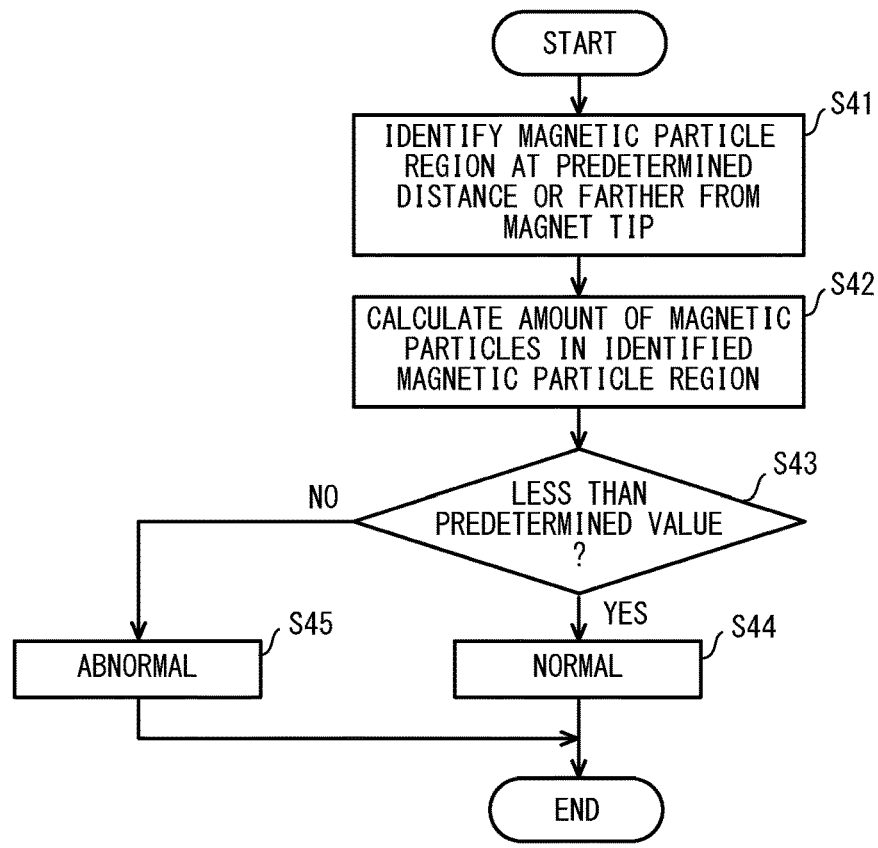
FIG. 13 is a flow chart for explaining a process of detecting the remaining state of the magnetic particles in the flow path of the analyzer.

With reference to FIG. 13, a process of detecting the remaining state of the magnetic particles in the flow path is described.

In step S41, the controller 115 identifies a magnetic particle region that is at a predetermined distance or farther from the tip of the magnet unit 80. In step S42, the controller 115 calculates the amount of the magnetic particles in the identified magnetic particle region. Specifically, on the basis of the procedure of magnetic particle region detection shown in FIG. 11, the amount of the magnetic particles in the magnetic particle region is calculated.

In step S43, the controller 115 determines whether the amount of the magnetic particles is less than a predetermined value. When the amount of the magnetic particles is less than the predetermined value, the process is advanced to step S44. When the amount of the magnetic particle is greater than or equal to the predetermined value, the process is advanced to step S45. In step S44, the controller 115 determines that the remaining amount of the magnetic particles is small and that the state is normal. In step S45, the controller 115 determines that the remaining amount of the magnetic particles is large and that the state is abnormal.

(Description of Method for Quantitative Determination of Remaining Magnetic Particles)

Figure 14:
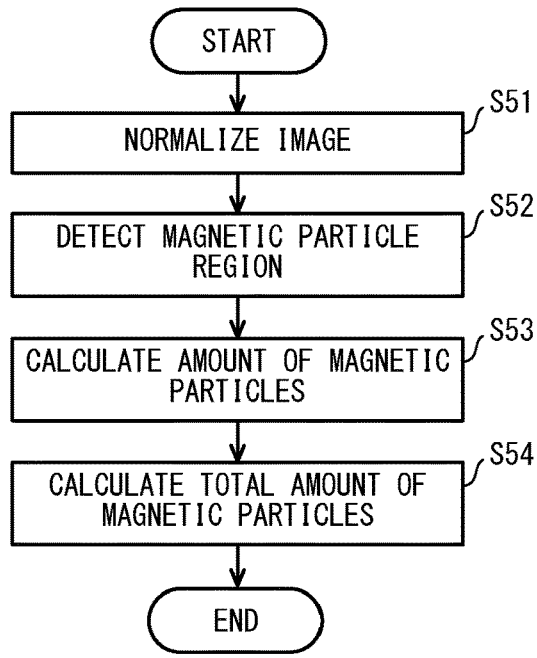
FIG. 14 is a flow chart for explaining a process of quantitative determination of remaining magnetic particles of the analyzer.

A method for quantitative determination of remaining magnetic particles based on image data of an image taken by the imaging unit 50 is described. With reference to FIG. 14, quantitative determination of remaining magnetic particles is described.

In step S51, the controller 115 performs normalization of a taken image. Specifically, normalization of white balance, exposure time, blurred image, distortion and the like of the image is performed. That is, normalization is performed by correcting factors that vary depending on the image-taking condition. For example, in a moving image, white balance and exposure time vary as a result of the magnet being moved and the image being varied. Thus, a region where the image does not vary in the moving image is obtained, and the entirety of the image is subjected to correction so that the color tone of the region does not change, whereby normalization of white balance and exposure time is performed. For example, the entirety of the image is subjected to multiplication by a correction value so that the median of each channel (RGB) of the region becomes 128. For blurred image correction, an established technology for camera shake correction may be used. For distortion by the imaging unit 50, an established distortion correction technology may be used.

In step S52, the controller 115 detects a magnetic particle region. For example, for the detection of a magnetic particle region, the method for magnetic particle region detection shown in FIG. 11 may be used.

In step S53, the controller 115 calculates the amount of the magnetic particles in each pixel in the image. For example, for the calculation of the amount of the magnetic particles, the method for detecting the amount of the magnetic particles shown in FIG. 11 may be used.

In step S54, the controller 115 calculates the total amount of the magnetic particles. Specifically, on the basis of the amount of the magnetic particles for each pixel in the magnetic particle region calculated in step S53, the total sum of these is obtained, whereby the total amount of the magnetic particles is calculated. Accordingly, the remaining magnetic particles can be quantitatively determined.

(Description of Method for Quantitative Determination of Magnetic Particle Agitation Efficiency)

A method for quantitative determination of magnetic particle agitation efficiency based on image data of an image taken by the imaging unit 50 is described.

Figure 15:
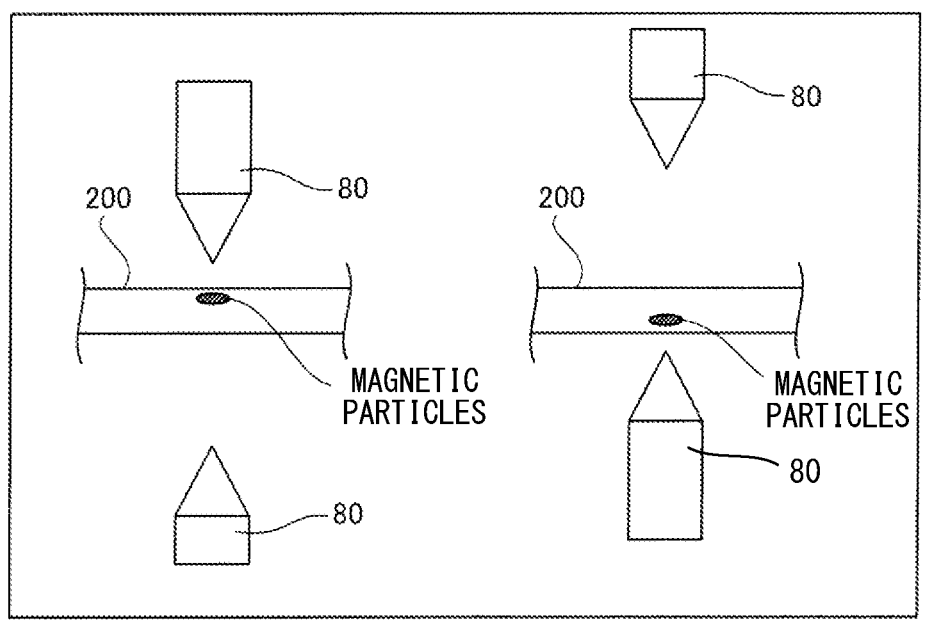
FIG. 15 is a diagram for explaining agitation operation performed by the magnet unit.

As shown in FIG. 15, by the magnet unit 80 being moved in the up-down direction relative to the specimen cartridge 200, the magnetic particles in the specimen cartridge 200 are alternately attracted in the upward direction and in the downward direction, whereby the liquid storage portion is agitated. That is, when the magnet unit 80 at the upper side is caused to approach the specimen cartridge 200, the magnetic particles move in the upward direction in the liquid storage portion. In this case, the magnet unit 80 at the lower side is moved away from the specimen cartridge 200. When the magnet unit 80 at the lower side is caused to approach the specimen cartridge 200, the magnetic particles move in the downward direction in the liquid storage portion. In this case, the magnet unit 80 at the upper side is moved away from the specimen cartridge 200. Then, as a result of the moving of the magnetic particles, the liquid in the liquid storage portion is moved to be agitated.

Figure 16:
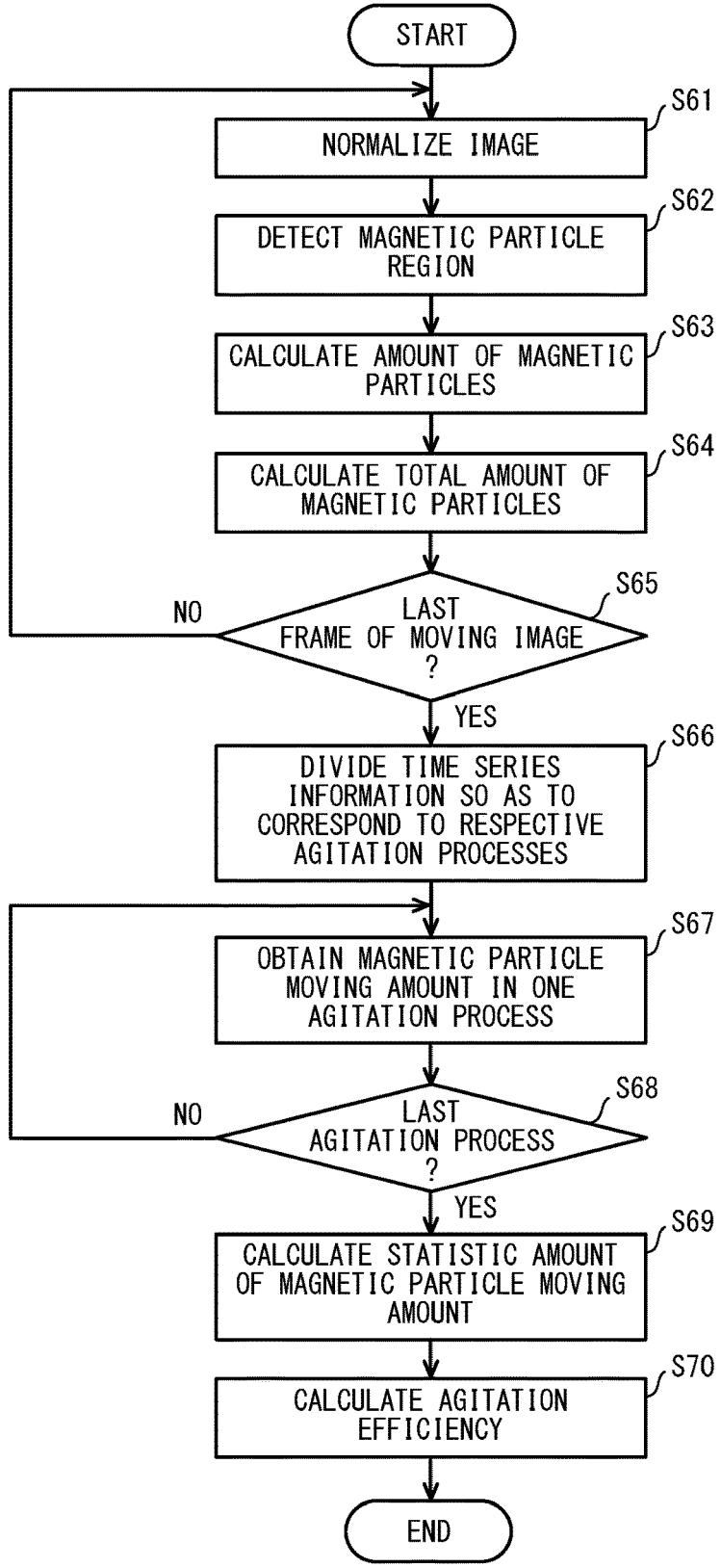
FIG. 16 is a flow chart for explaining a process of quantitative determination of magnetic particle agitation efficiency of the analyzer.

With reference to FIG. 16, quantitative determination of magnetic particle agitation efficiency is described.

In step S61, the controller 115 performs normalization of a taken image. Specifically, normalization of the taken image is performed in a similar manner to that in the step S51 shown in FIG. 14.

In step S62, the controller 115 detects a magnetic particle region. For example, for the detection of a magnetic particle region, the method for magnetic particle region detection shown in FIG. 11 may be used.

In step S63, the controller 115 calculates the amount of the magnetic particles in each pixel in the image. For example, the calculation of the amount of the magnetic particles, the method for detecting the amount of the magnetic particles shown in FIG. 11 may be used.

In step S64, the controller 115 calculates the total amount of the magnetic particles. Specifically, on the basis of the amount of the magnetic particles for each pixel in the magnetic particle region calculated in step S63, the total sum of these is obtained, whereby the total amount of the magnetic particles is calculated.

In step S65, the controller 115 determines whether the frame is the last frame of the moving image. When the frame is not the last frame, the process is returned to step S61, and when the frame is the last frame, the process is advanced to step S66.

In step S66, the controller 115 divides time series information so as to correspond to the respective agitation processes. Specifically, the time series information is divided for each one agitation in which the magnet unit 80 performs one reciprocation movement. In step S67, the controller 115 obtains the moving amount of the magnetic particles during one agitation process. Specifically, the difference between the maximum value and the minimum value of the amount of the magnetic particles during one agitation is calculated, and the difference is obtained as the moving amount.

In step S68, the controller 115 determines whether the agitation process is the last agitation process. When the agitation process is not the last agitation process, the process is returned to step S67. When the agitation process is the last agitation process, the process is advanced to step S69. In step S69, the controller 115 calculates the statistic amount of the magnetic particle moving amount. For example, the mean value, the median, or the like of the magnetic particle moving amount is calculated as the statistic amount. A large magnetic particle moving amount indicates moving of a large number of the magnetic particles, and indicates a state where the agitation is being performed in a good manner. Meanwhile, a small magnetic particle moving amount indicates moving of a small number of the magnetic particles, and indicates a state where the agitation is not being performed in a good manner.

In step S70, the controller 115 calculates agitation efficiency. Specifically, on the basis of the statistic amount of the magnetic particle moving amount, the agitation efficiency is calculated.

With respect to the analysis of the time series information, the amount of the magnetic particles at the upper face of the liquid storage portion may be calculated for each frame of the moving image, and the calculated amount of the magnetic particles may be associated with measurement time, thereby to obtain time series information. For example, in a case where the agitation state is normal, when the magnet unit 80 at the upper side is caused to approach the specimen cartridge 200, the amount of the magnetic particles at the upper face of the liquid storage portion increases. Meanwhile, when the magnet unit 80 at the lower side is caused to approach the specimen cartridge 200, the amount of the magnetic particles at the upper face of the liquid storage portion decreases. That is, when agitation is normally performed, the cycle in which the magnet unit 80 is moved in the up-down direction and the cycle of the increase/decrease of the detected magnetic particles are linked with each other. Accordingly, by comparing the moving cycle of the magnet unit with the cycle of increase/decrease of the detected magnetic particles, it is possible to quantitatively determine the magnetic particle agitation efficiency.

It should be noted that the embodiments disclosed herein are merely illustrative in all aspects and should not be considered as restrictive. The scope of the present disclosure is defined not by the description of the above embodiments but by the scope of the claims, and includes meaning equivalent to the scope of the claims and all changes within the scope.

What is claimed is:

1. An analysis method comprising:
moving a complex, by a magnet unit, in a flow path of a specimen cartridge which includes the flow path and a detection vessel, wherein the complex comprises a test substance binding to a magnetic particle and a label substance binding to the test substance;
taking an image of the magnetic particles at the detection vessel to obtain an amount of the magnetic particles successfully delivered;
detecting the label substance contained in the complex in the detection vessel; and
correcting a detection result of the label substance based on the amount of the magnetic particles obtained from the image of the magnetic particles.

2. The analysis method of claim 1, wherein
on the basis of image data of the taken image, a state of the magnetic particles in the specimen cartridge is obtained.

3. The analysis method of claim 2, wherein
on the basis of the image data of the taken image, whether the magnetic particles remain by not less than a predetermined amount at a place that is away from the magnet unit by not less than a predetermined distance, or whether the magnetic particles are normally agitated is obtained as the state of the magnetic particles in the specimen cartridge.

4. The analysis method of claim 2, wherein
on the basis of image data of a taken image of the detection vessel, whether the magnetic particles with which the complex is formed are being normally moved to the detection vessel is obtained as the state of the magnetic particles in the specimen cartridge.

5. The analysis method of claim 2, wherein
on the basis of a change in an amount of the magnetic particles in the image data of the taken image, whether the magnetic particles are being normally agitated by the magnet unit is obtained.

6. The analysis method of claim 2, wherein
on the basis of the image data of the taken image, mixture of a bubble into the flow path or into the detection vessel of the specimen cartridge is detected.

7. The analysis method of claim 2, wherein
on the basis of color information or contrast information of the image data of the taken image, the magnetic particles are detected.

8. The analysis method of claim 2, wherein
on the basis of the image data of the taken image, the flow path is detected, and the magnetic particles are detected in the detected flow path.

9. The analysis method of claim 2, wherein
on the basis of the obtained state of the magnetic particles in the specimen cartridge, an error is notified.

10. An analysis method comprising:
moving a complex, by a magnet unit, in a flow path of a specimen cartridge which includes the flow path and a detection vessel, wherein the complex comprises a test substance binding to a magnetic particle and a label substance binding to the test substance;
taking an image of the magnetic particles at the detection vessel to obtain a state of the magnetic particles successfully delivered;
detecting the label substance contained in the complex in the detection vessel; and
notifying an error based on the obtained state of the magnetic particles.

11. The analysis method of claim 10, wherein
on the basis of image data of the taken image, a state of the magnetic particles in the specimen cartridge is obtained.

12. The analysis method of claim 11, wherein
on the basis of the image data of the taken image, whether the magnetic particles remain by not less than a predetermined amount at a place that is away from the magnet unit by not less than a predetermined distance, or whether the magnetic particles are normally agitated is obtained as the state of the magnetic particles in the specimen cartridge.

13. The analysis method of claim 11, wherein
on the basis of image data of a taken image of the detection vessel, whether the magnetic particles with which the complex is formed are being normally moved to the detection vessel is obtained as the state of the magnetic particles in the specimen cartridge.

14. The analysis method of claim 13, wherein
an amount of the magnetic particles in the detection vessel is obtained from the image data of the taken image of the detection vessel, and a measurement result of the label of the labeled substance is corrected based on the obtained amount of the magnetic particles.

15. The analysis method of claim 11, wherein
on the basis of a change in an amount of the magnetic particles in the image data of the taken image, whether the magnetic particles are being normally agitated by the magnet unit is obtained.

16. The analysis method of claim 11, wherein
on the basis of the image data of the taken image, mixture of a bubble into the flow path or into the detection vessel of the specimen cartridge is detected.

17. The analysis method of claim 11, wherein
on the basis of color information or contrast information of the image data of the taken image, the magnetic particles are detected.

18. The analysis method of claim 11, wherein
on the basis of the image data of the taken image, the flow path is detected, and the magnetic particles are detected in the detected flow path.

* * * * *